United States Patent
Konno et al.

(10) Patent No.: US 9,611,458 B2
(45) Date of Patent: Apr. 4, 2017

(54) METHOD FOR PREPARING AQUEOUS SOLUTION CONTAINING CULTURE MEDIUM AND CHELATING AGENT

(75) Inventors: Yoshinobu Konno, Tokyo (JP); Kairo Wakamatsu, Tokyo (JP); Yasufumi Imamoto, Tokyo (JP); Jun Ishibashi, Tokyo (JP); Ken Takahashi, Tokyo (JP); Hisaya Tanaka, Tokyo (JP)

(73) Assignee: KYOWA HAKKO KIRIN CO., LTD, Tokyo (JP)

( * ) Notice: Subject to any disclaimer, the term of this patent is extended or adjusted under 35 U.S.C. 154(b) by 427 days.

(21) Appl. No.: 13/976,524

(22) PCT Filed: Dec. 27, 2011

(86) PCT No.: PCT/JP2011/080236
§ 371 (c)(1),
(2), (4) Date: Jun. 27, 2013

(87) PCT Pub. No.: WO2012/091023
PCT Pub. Date: Jul. 5, 2012

(65) Prior Publication Data
US 2013/0267684 A1    Oct. 10, 2013

(30) Foreign Application Priority Data
Dec. 27, 2010  (JP) ................................. 2010-290444

(51) Int. Cl.
| | | |
|---|---|---|
| C12N 5/071 | (2010.01) | |
| C12N 5/00 | (2006.01) | |
| C12P 21/00 | (2006.01) | |
| B01D 61/14 | (2006.01) | |
| C07K 16/00 | (2006.01) | |
| C12N 1/38 | (2006.01) | |

(52) U.S. Cl.
CPC ........... *C12N 5/0682* (2013.01); *B01D 61/14* (2013.01); *C07K 16/00* (2013.01); *C12N 1/38* (2013.01); *C12N 5/0018* (2013.01); *C12P 21/005* (2013.01); *B01D 2311/04* (2013.01); *B01D 2311/2642* (2013.01); *C12N 2500/24* (2013.01); *C12N 2500/38* (2013.01); *C12N 2500/76* (2013.01); *C12N 2511/00* (2013.01)

(58) Field of Classification Search
CPC .............. C12N 5/0682; C12N 2500/24; C12N 2500/30; C12N 5/0018; C12P 21/005; B01D 2311/2692; B01D 61/14; B01D 2311/2642
See application file for complete search history.

(56) References Cited

U.S. PATENT DOCUMENTS

| | | | | |
|---|---|---|---|---|
| 4,466,889 A * | 8/1984 | Miller | ...................... | C08K 5/09 166/246 |
| 5,316,938 A * | 5/1994 | Keen | .................. | C07K 16/2893 435/404 |
| 5,508,196 A | 4/1996 | Mannweiler et al. | | |
| 5,772,646 A | 6/1998 | Blaney et al. | | |
| 6,048,728 A * | 4/2000 | Inlow | ..................... | C12N 5/005 435/325 |
| 6,103,529 A * | 8/2000 | Price | .................... | C12N 5/0043 435/325 |
| 7,390,660 B2 | 6/2008 | Behrendt et al. | | |
| 2008/0254513 A1 | 10/2008 | Cayli | | |
| 2009/0298976 A1 | 12/2009 | Yano et al. | | |
| 2012/0219588 A1* | 8/2012 | Thompson | ............... | C12N 7/00 424/211.1 |

FOREIGN PATENT DOCUMENTS

| | | |
|---|---|---|
| DE | 4215339 C1 | 4/1993 |
| EP | 0 073 599 A1 | 3/1983 |
| EP | 0 481 791 A2 | 4/1992 |
| JP | 7-506492 A | 7/1995 |
| JP | 2000-217455 A | 8/2000 |

(Continued)

OTHER PUBLICATIONS

Mercille, Sylvain, et al., "Filtration-Based Perfusion of Hybridoma Cultures in Protein-Free Medium: Reduction of Membrane Fouling by Medium Supplementation with DNase I", Biotechnology and Bioengineering, Apr. 15, 1994, pp. 833-846, vol. 43, No. 9.
Search Report, Issued by the European Patent Office, Dated Dec. 3, 2014, in counterpart European application No. 11854382.6.
Reichert, Janice, et al., "Monoclonal antibodies market," Nature Reviews, Drug Discovery, vol. 3, May 2004, pp. 383-384.
Hay, R.J., et al., "Mycoplasma infection of cultured cells," Nature Publishing Group, vol. 339, Jun. 8, 1989, pp. 487-488.
Fleurence, Rachael, et al., "Cost-Effectiveness of Biologic Agents for Treatment of Autoimmune Disorders: Structured Review of the Literature," The Journal of Rheumatology, vol. 33, No. 11, Nov. 2006, pp. 2124-2131.
"Filter Sterilization of Samples (1-100 mL) in Sterile Acrodisc® Syringe Filters 4.5.3," Pall Corporation, 4 pages.

(Continued)

*Primary Examiner* — Daniel C Gamett
(74) *Attorney, Agent, or Firm* — Sughrue Mion, PLLC

(57) ABSTRACT

Provided are a method for preparing a highly versatile aqueous solution having remarkably improved membrane filterability, which can be stably membrane-filtered in a short time, an aqueous solution prepared by the preparation method, a method for culturing cells using the aqueous solution which is prepared by the preparation method, a method for producing a physiologically active substance using the culturing method, a physiologically active substance produced by the method for producing a physiologically active substance, a method for performing membrane filtration of the aqueous solution which is prepared by the preparation method of the aqueous solution, a method for improving membrane filterability of the aqueous solution, and a method for producing the physiologically active substance by preparing the aqueous solution, performing membrane filtration of the aqueous solution, and then culturing cells using the resulting aqueous solution. The present invention relates to a method for preparing an aqueous solution, characterized by addition of a chelating agent.

18 Claims, 3 Drawing Sheets

(56) References Cited

FOREIGN PATENT DOCUMENTS

| JP | 2003-250533 A | 9/2003 |
|---|---|---|
| JP | 2006-500931 A | 1/2006 |
| WO | 2004/029069 A2 | 4/2004 |
| WO | 2010/036774 A1 | 4/2010 |

OTHER PUBLICATIONS

Imamoto, Yasufumi, et al., "Optimizing culture medium preparation process by DOE for sterilizing filtration," The 23rd Annual and International Meeting of the Japanese Association for Animal Cell Technology, Sep. 2010, p. 127.

Williams, James Earl, "Relationship of Sialic Acid to Dental Caries," Journal of Dental Research, vol. 46, No. 3, May 1967, pp. 514-521.

Communication dated Jul. 15, 2016, issued by the European Patent Office in European Patent Application No. 11854382.6.

Communication dated Nov. 11, 2016, issued by the European Patent Office in corresponding European application No. 11854382.6.

* cited by examiner

METHOD FOR PREPARING AQUEOUS SOLUTION CONTAINING CULTURE MEDIUM AND CHELATING AGENT

TECHNICAL FIELD

The present invention relates to a method for preparing an aqueous solution including a culture medium and a chelating agent, an aqueous solution prepared by the preparation method, a method for culturing cells using the aqueous solution which is prepared by the preparation method, a method for producing a physiologically active substance using the culturing method, a physiologically active substance produced by the method for producing a physiologically active substance, a method for performing membrane filtration of the aqueous solution which is prepared by the preparation method of the aqueous solution, a method for improving the membrane filterability of the aqueous solution, or a method for producing the physiologically active substance by preparing the aqueous solution, performing membrane filtration of the aqueous solution, and then culturing cells using the aqueous solution.

BACKGROUND ART

Physiologically active substances, in particular, glycoproteins or antibodies have been recently approved as various kinds of biopharmaceuticals, and more candidate substances are currently under development (Non-Patent Literature 1). For this reason, it is expected that production of physiologically active substances such as glycoproteins, antibodies or the like using cells will be more actively performed.

With respect to preparation of an aqueous solution for cell culture which is essential for the production of these physiologically active substances using cells, sterilization of a culture medium is required to ensure product and process safety. Until now, a 0.2 μm membrane filtration process has been widely used for removing microorganisms in the preparation of the aqueous solution for cell culture. In recent years, a 0.1 μm membrane filtration process has been proposed for mycoplasma removal (Non-Patent Literature 2). Therefore, excellent membrane filterability of the aqueous solution for cell culture is increasingly required and it is a problem.

Compared to small-molecule drugs, biopharmaceuticals require high production costs, which is also a problem faced by pharmaceutical industries (Non-Patent Literature 3). So far, efforts to reduce the cost has been made by achieving productivity improvement resulting from enhancement of some components and addition or enrichment of new components of the aqueous solution for cell culture, but on the other hand, the difficulty of achieving the excellent membrane filterability of the aqueous solution is increasing. Because of restrictions on facilities and scale-up of production equipments to meet market needs, there is also a need for highly versatile aqueous solutions for cell culture which can be more stably membrane-filtered in a short time.

Alteration of filtration equipments, addition of filtration membrane or replacement of filtration membrane material, or improvement of dissolution conditions such as temperature during preparation of the aqueous solution for cell culture have been tried to improve the amount of membrane filtrate or membrane filterability of the aqueous solution (Patent Literature 1, Non-Patent Literatures 4 and 5). However, the improvement of membrane filterability of the aqueous solution for cell culture by increasing the membrane area is not industrially preferred in terms of restrictions on costs and facilities. Further, the improvement of dissolution conditions did not bring about remarkable improvement of membrane filterability of the aqueous solution for cell culture.

Chelating agents such as citric acid, malic acid, ethylenediaminetetraacetic acid or the like have been widely known as one of the components contained in the aqueous solution for cell culture (Patent Literatures 2 and 3). Sialic acid is also known as a substance having a chelating function (Non-Patent Literature 6). However, there have been no reports of a method for improving membrane filterability of the aqueous solution for cell culture by use of chelating agents.

PRIOR ART LITERATURES

Patent Literatures

[Patent Literature 1] Japanese Patent Publication No. Hei.-07-506492
[Patent Literature 2] Japanese Patent Publication No. 2003-250533
[Patent Literature 3] Japanese Patent Publication No. 2000-217455

Non-Patent Literatures

[Non-Patent Literature 1] Nature Reviews Drug Discovery, May 2004, Vol. 3, p. 383
[Non-Patent Literature 2] Nature, June 1989, Vol. 339, p. 487-488
[Non-Patent Literature 3] The Journal of Rheumatology, November 2006, Vol. 33, p. 2124-2131
[Non-Patent Literature 4] Pall Corporation, "Filter Sterilization of Samples (1-100 mL) in Sterile Acrodisc (Registered trademark) Syringe Filters.5.3", [online], [search Nov. 15, 2010], internet <http:// www.pall.com/variants/pdf/pdf/laboratory_49533.pdf>
[Non-Patent Literature 5] Book of Abstracts of The 23rd Annual and International Meeting of the Japanese Association for Animal Cell Technology, September 2010, p. 127
[Non-Patent Literature 6] Journal of Dental Research, May 1967, Vol. 46, No. 3, p. 514-521

DISCLOSURE OF THE INVENTION

Problems to be Solved by the Invention

Accordingly, in view of the above problems, the present invention provides a preparation method for an aqueous solution having remarkably improved filterability, an aqueous solution prepared by the preparation method, a method for culturing cells using the aqueous solution which is prepared by the preparation method, a method for producing a physiologically active substance using the culturing method, a physiologically active substance produced by the method for producing a physiologically active substance, a method for performing membrane filtration of the aqueous solution which is prepared by the preparation method of the aqueous solution, a method for improving the membrane filterability of the aqueous solution, or a method for producing the physiologically active substance by preparing the aqueous solution, performing membrane filtration of the aqueous solution, and then culturing cells using the aqueous solution.

Means for Solving the Problems

That is, the present invention is as follows.

1. A method for preparing an aqueous solution comprising a culture medium and a chelating agent, wherein the chelating agent is added to the aqueous solution prior to the final pH adjustment of the aqueous solution.

2. The method for preparing an aqueous solution described in 1 above, wherein the chelating agent is one or more selected from citric acid, malic acid, ethylenediaminetetraacetic acid, ethylenediaminetetraacetic acid iron (III) sodium salt, sialic acid, and salts or hydrates thereof.

3. The method for preparing an aqueous solution described in 1 or 2 above, wherein the culture medium is a powdered culture medium, a liquid culture medium, or a slurry culture medium.

4. The method for preparing an aqueous solution described in 3 above, wherein the powdered culture medium further includes one or more selected from metal salts, sugars, and vitamins.

5. The method for preparing an aqueous solution described in any one of 1 to 4 above, wherein the culture medium is a culture medium for cell culture.

6. The method for preparing an aqueous solution described in 5 above, wherein the culture medium is a culture medium for animal cells.

7. The method for preparing an aqueous solution described in 6 above, wherein the culture medium is a culture medium for Chinese hamster ovary tissue-derived CHO cells.

8. An aqueous solution which is prepared by the method described in any one of 1 to 7 above.

9. A method for culturing cells using the aqueous solution which is prepared by the method described in any one of 1 to 7 above.

10. The method for culturing cells described in 9 above, wherein the cells are animal cells.

11. The method for culturing cells described in 10 above, wherein the cells are Chinese hamster ovary tissue-derived CHO cells.

12. A method for producing a physiologically active substance using the method for culturing cells described in any one of 9 to 11 above.

13. The method for producing a physiologically active substance described in 12 above, wherein the physiologically active substance is a peptide or a protein.

14. The method for producing a physiologically active substance described in 13 above, wherein the protein is a glycoprotein or an antibody.

15. A physiologically active substance which is produced by the method for producing a physiologically active substance described in any one of 12 to 14 above.

16. A method for performing membrane-filtration of an aqueous solution comprising a culture medium and a chelating agent, wherein the aqueous solution is prepared by addition of a chelating agent prior to the final pH adjustment of the aqueous solution.

17. The method for performing membrane-filtration described in 16 above, wherein the chelating agent is one or more selected from citric acid, malic acid, ethylenediaminetetraacetic acid, ethylenediaminetetraacetic acid iron (III) sodium salt, sialic acid, and salts or hydrates thereof.

18. The method for performing membrane-filtration described in 16 or 17 above, wherein the culture medium is a powdered culture medium, a liquid culture medium, or a slurry culture medium.

19. The method for performing membrane-filtration described in 18 above, wherein the powdered culture medium further includes one or more selected from metal salts, sugars, and vitamins.

20. The method for performing membrane-filtration described in any one of 16 to 19 above, wherein the culture medium is a culture medium for cell culture.

21. The method for performing membrane-filtration described in 20 above, wherein the culture medium is a culture medium for animal cells.

22. The method for performing membrane-filtration described in 21 above, wherein the culture medium is a culture medium for Chinese hamster ovary tissue-derived CHO cells.

23. The method for performing membrane-filtration described in any one of 16 to 22 above, wherein the membrane filter used in membrane filtration has a pore size of 1 nm to 100 μm.

24. A method for improving membrane filterability of an aqueous solution, which comprises adding a chelating agent to the aqueous solution to prepare the aqueous solution including the chelating agent, and performing membrane filtration of the aqueous solution.

25. The method for improving membrane filterability of an aqueous solution described in 24 above, which further comprises adding a culture medium to the aqueous solution to prepare the aqueous solution including the culture medium and the chelating agent, and performing membrane filtration of the aqueous solution.

26. The method for improving membrane filterability of an aqueous solution described in 24 or 25 above, wherein the chelating agent is added to the aqueous solution to prepare the aqueous solution including the chelating agent prior to the final pH adjustment of the aqueous solution.

27. The method for improving membrane filterability of an aqueous solution described in any one of 24 to 26 above, wherein the chelating agent is added to the aqueous solution prior to the addition of the culture medium, or together with the culture medium simultaneously.

28. A method for producing a physiologically active substance, which comprises adding a chelating agent to an aqueous solution to prepare the aqueous solution including a culture medium and the chelating agent prior to the final pH adjustment, performing membrane filtration of the aqueous solution, and then culturing cells using the resulting aqueous solution.

Effect of the Invention

Surprisingly, the present inventors have found for the first time that membrane filterability of an aqueous solution can be greatly improved by adding a chelating agent in a preparation method of the aqueous solution. The present inventors have also found that the chelating agent improves the membrane filterability in a concentration-dependent manner in the preparation method of the aqueous solution.

Further, the present inventors have found that membrane filterability of the aqueous solution can be greatly improved by adding the chelating agent prior to final pH adjustment of the aqueous solution in the preparation method of the aqueous solution. Furthermore, the present inventors have found that a physiologically active substance can be produced by culturing cells using the aqueous solution which is prepared by adding the chelating agent prior to final pH adjustment of the aqueous solution.

Based on these findings, it was shown that a method for preparing an aqueous solution including a culture medium and a chelating agent can be provided. Further, it was shown that an aqueous solution prepared by the preparation method, a method for culturing cells using the aqueous solution which is prepared by the preparation method, a method for producing a physiologically active substance using the method for culturing cells, and a physiologically active substance produced by the method for producing the physiologically active substance can be provided.

Furthermore, it was shown that a method for performing membrane filtration of the aqueous solution which is prepared by the preparation method of the aqueous solution and a method for improving membrane filterability of the aqueous solution, characterized in that the aqueous solution is prepared using a chelating agent can be provided. It was also shown that a method for producing the physiologically active substance by performing membrane filtration of the aqueous solution which is prepared by the preparation method and then culturing cells using the resulting aqueous solution can be provided.

EMBODIMENTS FOR CARRYING OUT THE INVENTION

Figure 1:
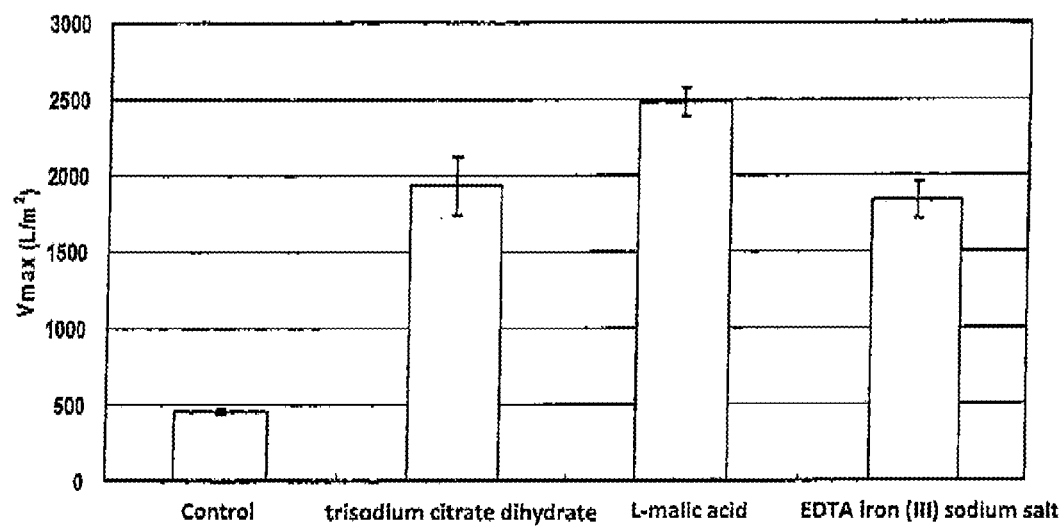
FIG. 1 shows that filterability of an aqueous solution is improved by adding a chelating agent, in which the vertical axis represents the maximum processing amount per unit membrane area [Vmax ($L/m^2$)], and the horizontal axis represents the chelating agent used.

Hereinafter, the present invention will be described in detail.

The present invention relates to a method for preparing an aqueous solution including a culture medium and a chelating agent, in which the chelating agent is added to the aqueous solution prior to final pH adjustment of the aqueous solution.

The aqueous solution is, but not particularly limited to, preferably an aqueous solution capable of culturing cells or the like (also referred to as an aqueous solution for cell culture).

The culture medium may be exemplified by a powdered culture medium, a liquid culture medium, or a slurry culture medium. The culture medium may be appropriately selected from the commercially available culture media, or a mixture of two or more thereof may be used. Further, the known culture medium described in the literatures may be selected.

Further, the culture medium may be exemplified by a culture medium for culturing bacterial cells, a culture medium for culturing yeast cells, a culture medium for culturing plant cells, a culture medium for culturing animal cells or the like. Among them, the culture medium for culturing animal cells is preferred. In addition, the culture medium may be but is not particularly limited to, for example, an expansion culture medium, a basal (initial) culture medium, a feed culture medium or the like.

Further, the culture medium may be any one of a synthetic culture medium, a semi-synthetic medium, or a natural culture medium. For example, it may include a basal culture medium, a serum-containing culture medium, a serum-free culture medium, a culture medium containing no animal-derived components, a protein-free culture medium or the like. Among them, the serum-free culture medium, the protein-free culture medium, or the fully synthetic culture medium is preferred.

The culture medium for cell culture is preferably a culture medium for culturing animal cells, and more preferably a culture medium for culturing Chinese hamster ovary tissue-derived CHO cells.

Examples of the basal culture medium may include commercially available culture medium of each company such as an RPMI1640 culture medium [The Journal of the American Medical Association, 199, 519 (1967)], an Eagle's MEM culture medium [Science, 122, 501 (1952)], a Dulbecco's Modified MEM (DMEM) culture medium [Virology, 8, 396 (1959)], an 199 culture medium [Proceeding of the Society for the Biological Medicine, 73, 1 (1950)], an F12 culture medium (manufactured by LTD [Proc. Natl. Acad. Sci. USA, 53, 288 (1965)], an Iscove's Modified Dulbecco's Medium (IMDM culture medium) [J. Experimental Medicine, 147, 923 (1978)], an EX-CELL (registered trademark) 302 culture medium, an EX-CELL (registered trademark) 325 culture medium (manufactured by SAFC bioscience) or an CHO-S-SFMII culture medium (manufactured by Invitrogen), or modified culture media thereof, or mixtures thereof, or the like. Among them, the RPMI1640 culture medium, the DMEM culture medium, the F12 culture medium, the IMDM and the EX-CELL (registered trademark) 302 culture medium, or the hybridoma SFM culture medium (manufactured by Invitrogen) are preferred.

The serum-containing culture medium may include, for example, those prepared by addition of one or more sera or serum fractions selected from sera of mammals such as cattle, horse or the like, sera of birds such as chicken or the like, sera of fish such as yellowtail or the like, and fractions thereof, to the basal culture medium.

Examples of the serum-free culture medium may include those prepared by adding to the basal medium, nutritional factors, physiologically active substances or the like as alternatives to serum In the culture medium containing no animal-derived ingredients, substances may be added instead of animal-derived ingredients. Examples of the substances may include physiologically active substances prepared by genetic recombination, hydrolysates, lipids containing no animal-derived raw materials and the like.

Examples of the protein-free culture medium may include an ADPF medium (Animal derived protein free medium, manufactured by HyClone), a CD-Hybridoma culture medium (manufactured by Invitrogen), a CD-CHO culture medium (manufactured by Invitrogen), an IS-CD-CHO culture medium (manufactured by Irvine Scientific), an EX- CELL (registered trademark) CD-CHO culture medium (manufactured by SAFC bioscience) and the like.

The preparation method of the powdered culture medium is, but not particularly limited to, preferably a preparation method by a mixing process of dry ingredients using a disk mill, a ball mill, a pin mill or the like, or a preparation method by lyophilization of the aqueous solution prepared in advance.

The powdered culture medium includes a culture medium present in a granular form.

The preparation method of the powdered culture medium present in the granular form may include, but is not particularly limited to, for example, Advanced granulation Technology (registered trademark) or the like. In addition, the method may include a process of spraying a solution in which at least one material selected from the group consisting of a natural thickening agent, a synthetic thickening agent, a sugar and a fat are dissolved onto granulated ingredients, and drying it.

Desired nutritional factors may be appropriately selected and added to the culture medium. Further, the desired nutritional factors may be appropriately selected and used to constitute the culture medium. Examples of the nutritional factors may include carbon sources such as sugars or nitrogen sources such as amino acids. Specific examples thereof may include amino acids, metals, vitamins, sugars, salts, lipids, nucleic acids, physiologically active substances, fatty acids, organic acids, proteins, hydrolysates or the like. These compounds may form salts such as hydrochloride salts, sodium salts, potassium salts, ammonium salts or the like, and/or solvates such as hydrates or the like.

Examples of the amino acids may include, but is not particularly limited to, for example, L-alanine (Ala), L-arginine (Arg), L-asparagine (Asn), L-aspartic acid (Asp), L-cysteine (Cys), L-cystine, L-glutamic acid (Glu), L-glutamine glycine (Gly), L-histidine (His), L-isoleucine (Ile), L-leucine (Leu), L-lysine (Lys), L-methionine (Met), L-phenylalanine (Phe), L-proline (Pro), L-serine (Ser), L-threonine (Thr), L-tryptophan (Trp), L-valine (Val) and the like, and they are used alone or in combinations of two or more thereof. Further, salts such as hydrochloride salts thereof and sodium salts thereof, and/or solvates such as hydrates thereof may be used. They may be added as a peptide, and for example, L-alanyl-L-glutamine, L-alanyl-L-cysteine, or the like are exemplified.

Examples of the physiologically active substances may include insulin, transferrin, serum albumin, a serum fraction containing growth factors and the like.

Examples of the lipids may include cholesterol, linoleic acid, linolenic acid and the like. Further, salts such as hydrochloride salts thereof and sodium salts thereof and/or solvates such as hydrates thereof may be used.

The metal may include, but is not particularly limited to, for example, iron, manganese, zinc, molybdenum, vanadium, copper, cadmium, rubidium, cobalt, zirconium, germanium, nickel, tin, chromium, silicon or the like, and they may be used alone or in combination of two or more thereof. These metals may form salts such as hydrochloride salts, sulfate salts, sodium salts, potassium salts, ammonium salts or the like, and/or solvates such as hydrates or the like.

The sugar may be, but is not particularly limited to, any one of monosaccharides, oligosaccharides, or polysaccharides. The sugar may also include sugar derivatives such as deoxysugars, uronic acids, amino sugars, sugar alcohols or the like. Examples thereof may include glucose, mannose, galactose, fructose, ribose, arabinose, ribulose, erythrose, erythrulose, glyceraldehyde, dihydroxy acetone, sedoheptulose, maltose, lactose, sucrose or the like, and they may be used alone or in combination of two or more thereof. Salts thereof such as hydrochloride salts, sodium salts or the like, and/or solvates thereof such as hydrates or the like may be also used.

Examples of the vitamins may include, but is not particularly limited to, for example, d-biotin, D-pantothenic acid, choline, folate, myo-inositol, niacinamide, pyridoxal, riboflavin, thiamine, cyanocobalamine, DL-α-tocopherol and the like, and they are used alone or in combinations of two or more thereof. Further, salts such as hydrochloride salts thereof and sodium salts thereof, and/or solvates such as hydrates thereof may be used.

The hydrolysate may be exemplified by hydrolysates of soy, wheat, rice, peas, cottonseed, fish or yeast extract, or extracts thereof. Specific example thereof may include SOY HYDROLYSATE UF (manufactured by SAFC Bioscience, Catalog No: 91052-1K3986 or 91052-5K3986).

The chelating agent is not particularly limited, as long as it meets the intended use of the aqueous solution prepared by adding the chelating agent. In addition, the chelating agent of the present invention may be used alone or a plurality of types of chelating agents may be used.

As the chelating agent, a water-soluble chelating agent is particularly preferred, and examples thereof may include aminocarboxylic acid-based, oxycarboxylic acid-based, lower dibasic carboxylic acid-based chelating agents, polyols, or inorganic compounds. Also, the chelating agent of the present invention may form salts or the like as long as it maintains the chelating effect, and for example, it may form salts such as hydrochloride salts, sodium salts, potassium salts, ammonium salts or the like, and/or solvates such as hydrates or the like.

Specific examples of the aminocarboxylic acid-based chelating agent may include nitrilotriacetic acid (NTA), N-hydroxyethyliminodiacetic acid (NIMDA), ethylenediaminediacetic acid (EDDA), ethylenediaminetetraacetic acid (EDTA), ethylenediaminetetraacetic acid iron(III) sodium salt (EDTA iron(III) sodium salt), N-hydroxyethyl-ethylenediaminetetraacetic acid (HEDTA), diethylenetriarninepentacetic acid (DTPA), 1,2 cyclohexanediaminetetraacetic acid (CyDTA), trimethylenediaminetetraacetic acid (TMTA), ethyleneglycol diethyl ether diamine tetraacetic acid (GEDTA), ethylenediaminetetrapropionic acid (EDTP), glutamic acid-N,N-diacetic acid, aspartic acid-N,N-diacetic acid, glycine, alanine, salts thereof, and/or solvates thereof such as hydrates or the like.

Specific examples of the oxycarboxylic acid-based chelating agent may include lactic acid, glycolic acid, citric acid, malic acid, tartaric acid, gluconic acid, mandelic acid, salts thereof, and/or solvates thereof such as hydrates or the like. Examples of the lower dibasic carboxylic acid-based chelating agent may include oxalic acid, malonic acid, salts thereof, and/or solvates thereof such as hydrates or the like.

Examples of the polyol may include glycols such as ethylene glycol, diethylene glycol, triethylene glycol or the like, or sugar alcohols. Specific examples thereof may include other inositols such as glycerin, erythrite, arabite, xylite, sorbite, mannite, galactite or the like.

Examples of the inorganic compound-based chelating agent may include pyrophosphoric acid, triphosphoric acid, condensed phosphoric acid, salts thereof, and/or solvates thereof such as hydrates or the like. Particularly, the preferred chelating agent is trisodium citrate dihydrate, L-malic acid or ethylenediaminetetraacetic acid iron(III) sodium salt.

Furthermore, sialic acid may be used as the chelating agent. Sialic acid means 2-keto-3-deoxynonic acid having a 9-carbon carboxylated skeleton, and is also known as neuraminic acid.

Sialic acid includes N-acetylneuraminic acid, N-glycolylneuraminic acid, O-acetylneuraminic acid, or deaminoneuraminic acid, or salts, hydrates and/or derivatives thereof.

Sialic acid includes those having 5-N-acetyl or 5-N-glycolylneuraminic acid as a backbone and several O-acetylated hydroxyl groups. Particularly, the preferred sialic acid of the present invention is N-acetylneuraminic acid dihydrate.

The chelating agent may be prepared by a chemical synthetic method publicly known.

The chelating agent is added during the preparation of the aqueous solution, and in particular, preferably added to the aqueous solution prior to the final pH adjustment. In the preparation method of the aqueous solution of the present invention, the order of adding the chelating agent to the aqueous solution (timing of addition) may be appropriately determined depending on the composition of the culture medium to be added, the kind of the chelating agent or the like, if added before the final pH adjustment of the aqueous solution. The membrane filterability of the prepared aqueous solution can be improved by adding the chelating agent to the aqueous solution prior to the final pH adjustment of the aqueous solution.

In the preparation method of the aqueous solution of the present invention, the chelating agent can be added to the aqueous solution together with any culture medium simultaneously, or before or after addition of the culture medium. Preferably, the chelating agent can be added to the aqueous solution before addition of the culture medium, or together with the culture medium simultaneously. The chelating agent may be also added to the culture medium in advance. The membrane filterability of the prepared aqueous solution can be further improved by adding the chelating agent to the aqueous solution before addition of the culture medium, or together with the culture medium simultaneously.

In the present invention, the final pH adjustment refers to a process of adjusting the pH of the aqueous solution to a predetermined pH. The final pH is adjusted depending on the intended use of the aqueous solution. When the aqueous solution is the aqueous solution for cell culture, the pH value may be any value as long as the cells can be cultured at the pH value. If pH adjustment is not required, final addition of the substances to the aqueous solution to be contained in the aqueous solution is regarded as the final pH adjustment.

The final pH adjustment may be carried out using any acid or alkali. Specific examples thereof may include sodium bicarbonate, hydrochloric acid, sodium hydroxide or the like.

An example of regarding the final addition of the substance to the aqueous solution to be contained in the aqueous solution as the final pH adjustment is buffering agents such as $Na_2CO_3$, 4-(2-hydroxyethyl)-1-piperazineethanesulfonic acid (HEPES), or 3-(N-Morpholino) propanesulfonic acid (MOPS) already contained in the culture medium to adjust the pH.

The addition amount of the chelating agent is not particularly limited, but it is preferred that such amount is added that the concentration of the added chelating agent in the aqueous solution after preparation of the aqueous solution is preferably 0.001 mmol/L or higher, more preferably 0.01 mmol/L or higher, much more preferably 0.1 mmol/L or higher, and particularly preferably 0.34 mmol/L or higher.

Further, the addition amount of the chelating agent in the aqueous solution may be appropriately selected by those skilled in the art within the range from 0.001 to 1000 mmol/L, from 0.01 to 100 mmol/L, from 0.1 to 100 mmol/L, and from 0.1 to 50 mmol/L, and such amount may also be added that the chelating agent is preferably from 0.34 to 89 mmol/L, more preferably from 0.34 to 15 mmol/L, and particularly preferably from 0.34 to 6.8 mmol/L. The concentration of the chelating agent in the prepared aqueous solution may be further increased by a metal (such as iron)-chelate complex which is added to the medium as a metal source of iron or the like.

In the preparation of the aqueous solution of the present invention, hydrolysates, metal salts, sugars, vitamins, amino acids, pH adjusting agents, organic acids, fatty acids, peptides, physiologically active substances, lipids, nucleic acids, or the like may be added separately or may be added in part after mixing with the culture medium. A mixture of metal salts, sugars or vitamins with the culture medium may be added.

The cells may be any of eukaryotic cells and prokaryotic cells, and examples thereof may include cells derived from mammals, birds, reptiles, amphibians, fish, insect, plants or the like, microorganisms such as bacteria, *E. coli, Bacillus subtilis* or the like, cells derived from microorganisms such as bacteria, *E. coli, Bacillus subtilis* or the like, or yeasts or yeast-derived cells or the like.

Among them, cells of animals belonging to mammals are preferred, animal cells derived from primates such as humans or monkeys, or animal cells derived from rodents such as mice, rats, or hamsters are more preferred, or Chinese hamster ovary tissue-derived CHO cells are most preferred.

The Chinese hamster ovary tissue-derived CHO cells of the present invention may be any cell line established from Chinese hamster (*Cricetulus griseus*) ovary tissue.

Specifically, for example, CHO cells described in the documents such as Journal of Experimental Medicine, 108, 945 (1958), Proc. Natl. Acad. Sci. USA, 60, 1275 (1968), Genetics, 55, 513 (1968), Chromosoma, 41, 129 (1973), Methods in Cell Science, 18, 115 (1996), Radiation Research, 148, 260 (1997), Proc. Natl. Acad. Sci. USA, 77, 4216 (1980), Proc. Natl. Acad. Sci. 60, 1275 (1968), Cell, 6, 121 (1975), Molecular Cellgenetics, Appendix I, II, 883-900.

Further, examples thereof may include CHO-K1 line (ATCC No. CCL-61), DUXB11 line (ATCC CRL-9096), Pro-5 line (ATCC CRL-1781), CHO/dhfr-(ATCC No. CRL-9096) registered in ATCC (The American Type Culture Collection), commercially available CHO-S cell line (Lifetechnologies Inc. Cat # 11619) or CHO/DG44 [Proc. Natl. Acad. Sci. USA, 77, 4216 (1980)], or sub-strains obtained by adapting these strains in various media.

Examples of the cells belonging to mammals may include myeloma cells, ovarian cells, renal cells, blood cells, uterine cells, connective tissue cells, mammary cells, embryonic retinoblastoma cells, or cells derived therefrom. Among them, cells selected from myeloma cells, myeloma cell-derived cells, ovarian cells, and ovarian cell-derived cells.

Examples thereof may include human cell lines such as HL-60 (ATCC No. CCL-240), HT-1080 (ATCC No. CCL-121), HeLa (ATCC No, CCL-2), 293 (ECACC No. 85120602), Narnalwa (ATCC CRL-1432), Namalwa KJM-1 [Cytotechnology, 1, 151 (1988)], NM-F9 (DSM ACC2605, International Publication WO 2005/017130) and PER.C6 (ECACC No. 96022940, U.S. Pat. No. 6,855,544), monkey cell lines such as VERO (ATCC No. CCL-1651) and COS-7

(ATCC No. CRL-1651), mouse cell lines such as C127I (ATCC No. CRL-1616), Sp2/0-Ag14 (ATCC No. CRL-1581), and NIH3T3 (ATCC No. CRL-1658), NS0 (ATCC No. CRL-1827), rat cell lines such as Y3 Ag 1.2.3. (ATCC No. CRL-1631), YO (ECACC No. 85110501) and YB2/0 (ATCC No. CRL-1662), hamster cell lines such as Chinese hamster ovary tissue-derived CHO cells described above and BH-K21 (ATCC No. CRL-10), dog cells such as MDCK (ATCC No. CCL-34), and the like.

Examples of the cells belonging to the bird may include a chicken cell line SL-29 (ATCC No. CRL-29), and the like. Examples of the cells belonging to the fish may include a zebra fish cell line ZF4 (ATCC No. CRL-2050), and the like.

Examples of the cells belonging to the insect may include a moth (*Spodoptera frugiperda*) cell line Sf9 (ATCC No. CRL-1711) and the like. Examples of the primary culture cells used in the vaccine production may include primary monkey kidney cells, primary rabbit kidney cells, primary chicken embryonic cells, primary quail embryonic cells and the like.

Examples of the myeloma cell or myeloma cell-derived cells may include Sp2/0-Ag14, NS0, Y3 Ag 1.2.3., YO or YB2/0 and the like. Examples of the ovarian cells or ovarian cell-derived cells may include Chinese hamster ovary tissue-derived CHO cells described above and the like. Further, Examples of the renal cells may include 293, VERO, COS-7, BHK21, MDCK and the like.

Examples of the blood cells may include HL-60, Namalwa, Namalway KJM-1, NM-F9 and the like. Examples of the uterine cells may include HeLa and the like. Examples of the connective tissue cells may include HT-1080, NIH3T3 and the like. Examples of the mammary cells may include C1271I and the like. Examples of the embryonic retinoblastoma cells may include PER.C6 and the like, respectively.

The cells may be, but the presence or absence of their ability to produce the substance is not particularly limited, for example, iPS cells obtained by introducing the several genes to somatic cells, sperms or ova cells collected from a donor mammal including humans, cells producing substances, and fusion cells producing substances or the like.

Among them, cells producing substances or fusion cells producing substances are preferred. Animal cells producing substances, fusion cells derived from animals producing substances, or the like are more preferred. For example, when the desired substance is an antibody, hybridoma which is a fusion cell of myeloma cells and antibody-producing cells such as B cells or the like may be exemplified. Also, animal cells producing substances by mutation treatment, animal cells treated with mutations for increasing expression level of the substances, or the like are included in the animal cells.

Examples of the animal cells that are mutated to produce the substance may include cells in which mutations are introduced in protein modification enzymes in order to produce the desired substance or the like. For example, if the desired substance is a glycoprotein, cells in which mutations are introduced in a variety of sugar chain modification enzymes in order to change the structure of sugar chains, or the like may be exemplified.

In addition, the animal cells producing the substance may be any animal cells, as long as they are able to produce the desired substance. For example, animal cells that are transformed with a recombinant vector containing a gene involved in the production of substances are included. The transformant cells can be obtained by introducing a recombinant vector containing DNA and a promoter involved in the production of the substance into cells belonging to mammals above.

For the DNA involved in the production of the substance, for example, any one of DNA encoding a substance such as peptides or the like, and DNA encoding an enzyme or a protein which is involved in the biosynthesis of the substance and the like may be used.

For the promoter, any one of the promoters that function in the animal cells used in the present invention may be used, and examples thereof may include a promoter of immediate early (IE) gene of cytomegalovirus (CMV), a SV40 early promoter, a retroviral promoter, a metallothionein promoter, a heat shock promoter, a SRα promoter and the like. An enhancer of IE gene of human CMV or the like may be also used, together with the promoter.

The recombinant vector may be prepared using the desired vector. For the vector used for the preparation of the recombinant vector, any one of the vectors that function in the animal cells used in the present invention may be used. Examples thereof may include pcDNAI, pcDM8 (manufactured by Funakoshi), pAGE107 [JP Patent Publication No. H3-22979, Cytotechnology, 3, 133 (1990)], pAS3-3 (JP Patent Publication No. 112-227075), pcDM8 [Nature, 329, 840 (1987)], pcDNAI/Amp (manufactured by Invitrogen), pREP4 (manufactured by Invitrogen), pAGE103 [J. Biochem., 101, 1307 (1987)], pAGE210 and the like.

For the introduction method of recombinant vector into host cells, any method may be used, as long as it is able to introduce DNA into the host cells, and examples thereof may include electroporation (Cytotechnology, 3, 133 (1990)), a calcium phosphate method [JP Patent Publication No. H2-227075], lipofection [Proc. Natl. Acad. Sci. USA, 84, 7413 (1987), Virology, 52, 456 (1973)] and the like.

Specific examples of the transformed cells may include anti-GD3 human chimeric antibody-producing transformed cell 7-9-51 (FERM BP-6691), anti-CCPR chimeric antibody-producing transformed cell KM2760 (FERM BP-7054), anti-CCR4 humanized antibody-producing transformed cell KM8759 (FERM BP-8129) and KM8760 (FERM BP-8130), 709 LCA-500D (FERM BP-8239), anti-IL-5 receptor α chain chimeric antibody-producing transformed cell KM7399 (FERM BP-5649), anti-IL-5 receptor a chain human CDR-grafted antibody-producing transformed cell KM8399 (FERM BP-5648) and KM9399 (FERM BP-5647), anti-GM2 human CDR-grafted antibody-producing transformed cell KM8966 (FERM BP-5105), KM8967 (FERM BP-5106), KM8969 (FERM BP-5527), KM8970 (FERM BP-5528), anti-CD20 antibody-producing transformed cell line Ms704-CD20 (FERM BP-10092), anti-thrombin III-producing transformed cell Ms705-pKAN-ATIII (FERM BP-8472) and the like.

The present invention relates to an aqueous solution which is prepared by the method for preparing the aqueous solution including the culture medium and the chelating agent, characterized in that the chelating agent is added prior to the final pH adjustment of the aqueous solution.

Further, the present invention relates to a method for culturing cells using the aqueous solution which is prepared by the method for preparing the aqueous solution including the culture medium and the chelating agent, characterized in that the chelating agent is added prior to the final pH adjustment of the aqueous solution.

Examples of the method for culturing cells may include batch culture, repeated batch culture, fed-batch culture, perfusion culture or the like. The method for culturing cells may be any method as long as it is suitable for the cells used, and fed-batch culture is preferred.

Specifically, the culturing is typically carried out, for example, under the conditions of pH 6 to 8, from 30 to 40° C., for example, for 3 to 20 days in fed-batch culture or for 3 to 60 days in perfusion culture. During the culture, if necessary, antibiotics such as streptomycin or penicillin may be also added to the culture medium. In addition, for dissolved oxygen concentration control, pH control, temperature control, agitation, or the like, the method typically used in cell culture can be used.

A storage method of the aqueous solution is not particularly limited, as long as it is a method of maintaining the aqueous solution under aseptic conditions, for example, a method using a stainless steel tank, a disposable bag, or the like.

The culture method may be carried out in any culture volume, for example, in a minute culture volume of from 0.1 mL to 10 mL typically using a cell culture plate, in a small culture volume of from 10 to 1000 mL typically using a Erlenmeyer flask, or in even a large culture volume of from 1 to 20000 L for commercial production typically using a culture vessel or the like such as jars.

Further, the present invention relates to a method for producing a physiologically active substance comprising culturing cells using the aqueous solution including the culture medium and the chelating agent, which is prepared by adding the chelating agent prior to the final pH adjustment of the aqueous solution.

If the physiologically active substance which is produced by the method for producing the physiologically active substance of the present invention is a peptide or a protein, a direct expression method of producing the peptide or the protein in a host cell, a method of producing and secreting the peptide or the protein outside the host cells or the like (Molecular Cloning, Second Edition) may be used.

The peptide or protein can be actively secreted out of the host cells by using the method of Paulson et al. [J. Biol. Chem., 264, 17619 (1989)], the method of Lowe et al. [Proc. Natl. Acad. Sci. USA, 86, 8227 (1989), Genes Develop., 4, 1288 (1990)], or the method described in Japanese Patent Publication No. Hei.-05-336963, or International Publication No. 94/23021. In other words, the desired peptide or protein can be actively secreted outside the host cells by expressing it in the form of combining the signal peptide at the N-terminus of the desired peptide or protein using a gene recombination method.

Further, production amount of the desired peptide or protein can be increased by using a gene amplification system using a dihydrofolate reductase gene described in Japanese Patent Publication No. Hei.-02-227075, or the like.

The desired peptide or protein produced by the method of the present invention may be isolated and purified, for example, using a typical method of isolating and purifying a peptide or protein.

After completion of the culture, if the desired peptide or protein is expressed in a dissolved state inside the cell, the cells are harvested by centrifugation, suspended in an aqueous buffer, and disrupted using a sonicator, a French press, a Manton-Gaulin homogenizer, or a dynomill so as to obtain a cell-free extract.

It is possible to obtain a crude purified product or a purified product from the supernatant which can be obtained by centrifuging the cell-free extract using a typical method of isolating and purifying peptides or proteins, i.e., a solvent extracting, salting-out with ammonium sulfate, or the like, desalting, precipitation with organic solvents, anion exchange chromatography using resins such as diethylaminoethyl sepharose or DIAION HPA-75 (manufactured by Mitsubishi Chemical Corp.), cation exchange chromatography using resins such as S-sepharose FF (manufactured by Pharmacia), hydrophobic chromatography using resins such as butyl sepharose or phenyl sepharose, gel filtration using a molecular sieve, affinity chromatography using resins containing protein A, protein G, or the like, chromatofocusing, and electrophoresis such as isoelectric focusing, alone or in combination.

If the desired peptide or protein is secreted outside the cell, the peptide or protein can be recovered from the culture supernatant. That is, the culture supernatant is obtained by treating the culture with the method such as centrifugation as described above, and a crude purified product or a purified product can be obtained from the culture supernatant by the isolation and purification method as described above.

The physiologically active substance may be any substance as long as it can be produced by cells, preferably animal cells. A substance produced by cells of animal belonging to mammals is preferred. Examples of the substance may include amino acids, peptides, proteins, or biological catalyst molecules such as ribozymes, molecules for structural formation/retention such as keratin, collagen, elastin, resilin or fibroin, vaccines such as smallpox vaccine, polio vaccine, measles vaccine, rubella vaccine, mumps vaccine, rabies vaccine, varicella vaccine, bovine ephemeral fever vaccine, Ibaraki disease vaccine, or infectious bovine tracheitis vaccine, or viruses such as adenovirus or baculovirus, or the like.

The peptide is preferably peptides derived from eukaryotic cells, more preferably peptides derived from animal cells, and examples thereof may include peptides derived from mammalian cells. Further, the peptide may be in any form, as long as it includes the desired peptide and has the activity, and the peptide may be, for example, the artificially modified peptides such as fusion peptides prepared by fusion with other peptides and the like, or peptides composed of partial peptide fragments.

Example of the peptide may include a peptide of the partial fragments of glycoprotein, which maintains the activity of the glycoprotein. If the glycoprotein is an enzyme, a peptide to modulate the enzymatic activity, a peptide to keep the structure of the enzyme, or the like are also included. Specific examples of the peptide to modulate the enzymatic activity may include a peptide which acts as an agonist or antagonist of glycoprotein, or the like.

Any agonist may be used as the agonist, as long as it is a peptide having an activity of enhancing the glycoprotein activity, and specific example thereof may include somatostatin derivatives, somatropin, atrial natriuretic peptide, glucagon, insulin, insulin-like growth factor, gonadotropin and the like.

Any antagonist may be used as the antagonist, as long as it is a peptide having an activity of inhibiting the glycoprotein activity, and specific example thereof may include pegvisomant and the like.

The protein may be preferably a protein derived from a eukaryotic cell, and more preferably, a protein derived from an animal cell, for example, a protein derived from a mammalian cell. In addition, the protein may have any structure as long as it includes the desired protein and has the activity thereof. For example, the protein may be an artificially modified protein such as fusion protein fused with other protein, or a protein consisting of a partial fragment.

Specific examples of the protein may include glycoproteins, antibodies or the like.

Specific examples of the glycoprotein may include erythropoietin (EPO) [J. Biol. Chem., 252, 5558 (1977)], thrombopoietin (TPO) [Nature, 369 533 (1994)], a tissue-type plasminogen activator, pro-urokinase, thrombomodulin, antithrombin III, protein C, protein S, blood coagulation factor VII, blood coagulation factor VIII, blood coagulation factor IX, blood coagulation factor X, blood coagulation factor XI, blood coagulation factor XII, a prothrombin complex, fibrinogen, albumin, gonadotropic hormone, thyroid-stimulating hormone, epidermal growth factor (EGF), hepatocyte growth factor (HGF), keratinocyte growth factor, activin, osteogenic factor, stem cell factor (SCF), granulocyte colony stimulating factor (G-CSF) [J. Biol. Chem., 258, 9017 (1983)], macrophage colony stimulating factor (M-CSF) [J. Exp. Med., 173, 269 (1992)], granulocyte-macrophage colony stimulating factor (GM-CSF) [J. Biol. Chem., 252, 1998 (1977)], interferon α; interferon β, interferon γ, interleukin-2 (IL-2) [Science, 193, 1007 (1976)], interleukin 6, interleukin 10, interleukin 11, interleukin-12 (IL-12) [J. Leuc. Biol., 55, 280 (1994)], soluble interleukin 4 receptor, tumor necrosis factor α, DNaseI, galactosidase, a glucosidase, glucocerebrosidase, hemoglobin or transferrin, derivatives thereof, partial glycoprotein fragments thereof and the like.

Any antibody may be used, as long as it has an antigen-binding activity, and examples thereof may include antibodies recognizing tumor-associated antigens or antibody fragments thereof, antibodies recognizing allergy or inflammation-associated antigens or antibody fragments thereof, antibodies recognizing cardiovascular disease-associated antigens or antibody fragments thereof, antibodies recognizing autoimmune disease-associated antigens or antibody fragments thereof, antibodies recognizing viral or bacterial infection-associated antigens or antibody fragments thereof and the like.

Examples of tumor-associated antigens may include CD1a, CD2, CD3, CD4, CD5, CD6, CD7, CD9, CD10, CD13, CD19, CD20, CD21, CD22, CD25, CD28, CD30, CD32, CD33, CD38, CD40, CD40 ligand (CD40L), CD44, CD45, CD46, CD47, CD52, CD54, CD55, CD56, CD59, CD63, CD64, CD66b, CD69, CD70, CD74, CD80, CD89, CD95, CD98, CD105, CD134, CD137, CD138, CD147, CD158, CD160, CD162, CD164, CD200, CD227, adrenomedullin, angiopoietin related protein 4 (ARP4), aurora, B7-H1, B7-DC, integlin, bone marrow stromal antigen 2 (BST2), CA125, CA19.9, carbonic anhydrase 9 (CA9), cadherin, cc-chemokine receptor (CCR) 4, CCR7, carcinoembryonic antigen (CEA), cysteine-rich fibroblastgrowth factor receptor-1 (CFR-1), c-Met, c-Myc, collagen, CTA, connective tissue growth factor (CTGF), CTLA-4, cytokeratin-18, DF3, E-catherin, epidermal growth factor receptor (EGFR), EGFRvIII, EGFR2 (HER2), EGFR3 (HER3), EGFR4 (HER4), endoglin, epithelial cell adhesion molecule (EpCAM), endothelial protein C receptor (EPCR), ephrin, ephrin receptor (Eph), EphA2, endotheliase-2 (ET2), FAM3D, fibroblast activating protein (FAP), Fc receptor homolog 1 (FcrH1), ferritin, fibroblastgrowth factor8 (FGF8), FOPS receptor, basic FGF (bFGF), bFGF receptor, FGF receptor (FGFR) 3, FGFR4, FLT1, FLT3, folate receptor, frizzled homologue 10 (FZD10), frizzled receptor 4 (FZD-4), G250, G-CSF receptor, ganglioside (for example, GD2, GD3, GM2, GM3 or the like), globo H, gp75, gp88, GPR-9-6, heparinase 1, hepatocyte growth factor (HOF), HGF receptor, HLA antigen (for example, HLA-DR or the like), HM1.24, human milk fat globule (HMFG), hRS7, heat shock protein 90 (hsp90), idiotype epitope, insulin-like growth factor (IGF), IGF receptor (IGFR), interleukin (for example, IL-6, IL-15 or the like), interleukin receptor (for example, IL-6R, IL-15R or the like), integrin, immune receptor translocation associated-4 (IRTA-4), kallikrein 1, KDR, KIR2DL1, KIR2DL2/3, KS1/4, lamp-1, lamp-2, laminin-5, Lewis y, sialyl Lewis x, lymphotoxin-beta receptor (LTBR), LUNX, melanoma-associated chondroitin sulfate proteoglycan (MCSP), mesothelin, MICA, Mullerian inhibiting substance type II receptor (MISIIR), mucin, neural cell adhesion molecule (NCAM), Neal-5, Notchi, osteopontin, platelet-derived growth factor (PDGF), PDGF receptor, platelet factor-4 (PF-4), phosphatidylserine, Prostate Specific Antigen (PSA), prostate stem cell antigen (PSCA), prostate specific membrane antigen (PSMA), Parathyroid hormone related protein/peptide (PTHrP), receptor activator of NF-kappaB ligand (RANKL), receptor for hyaluronic acid mediated motility (RHAMM), ROBO1, SART3, semaphorin 4B (SEMA4B), secretory leukocyte protease inhibitor (SLPI), SM5-1, sphingosine-1-phosphate, tumor-associated glycoprotein-72 (TAG-72), transferrin receptor (TfR), TGF-beta, Thy-1, Tie-1, Tie2 receptor, T cell immunoglobulin domain and mucin domain 1 (TIM-1), human tissue factor (hTF), Tn antigen, tumor necrosis factor (TNF), Thomsen-Friedenreich antigen (TF antigen), TNF receptor, tumor necrosis factor-related apoptosis-inducing ligand (TRAIL), TRAIL receptor (for example, DR4, DRS or the like), system ASC amino acid transporter 2 (ASCT2), trkC, TROP-2, TWEAK receptor Fn14, type IV collagenase, urokinase receptor, vascular endothelial growth factor (VEGF), VEGF receptor (for example, VEGFR1, VEGFR2, VEGFR3 or the like), vimentin, VLA-4, and the like.

The antibody may be any one of monoclonal antibody or polyclonal antibody. Examples of the antibody class may include immunoglobulin G (IgG), immunoglobulin A (IgA), immunoglobulin E (IgE) and immunoglobulin M (IgM), and IgG is preferred. Further, examples of the IgG subclass may include IgG1, IgG2, IgG3 or IgG4.

The antibody may also include a fragment including a part of the antibody, or the like, and examples thereof may include Fab (Fragment of antigen binding), Fab', F(ab')$_2$, single chain Fv (scFv), disulfide stabilized Fv (dsFv), a fusion protein including an antibody Fc region and the like.

Examples of the antibody may include antibodies prepared by the genetic recombination technique, or the like, that is, antibodies obtained by introduction of an antibody gene inserted antibody-expressing vector into a host cell, in addition to antibodies produced by hybridoma cells that are prepared from spleen cells of an immunized animal after immunization of the animal with an antigen. Specific examples thereof may include an antibody produced by hybridoma, human chimeric antibody, humanized antibody, human antibody and the like.

The human chimeric antibody means an antibody which is composed of heavy-chain variable region (hereinafter, heavy chain is referred to as H chain, and variable region is referred to as V region, namely, HV or VH) and light-chain variable region (hereinafter, light chain is referred to as L chain, namely, LV or VL) of an antibody of a non-human animal, and heavy chain constant region (hereinafter, constant region is referred to as C region, namely, CH) and light chain constant region (hereinafter, referred to as CL) of a human antibody. As the non-human animal, any animal, for example, mice, rats, hamsters, rabbits or the like, may be used as long as it can be used to produce hybridoma.

The human chimeric antibody may be produced by obtaining cDNAs encoding VH and VL from a hybridoma capable of producing a monoclonal antibody, constructing a human chimeric antibody expression vector by inserting them into an expression vector for host cells having genes encoding human antibody CH and human antibody CL, and introducing them into host cells to express it.

The CH of the human chimeric antibody may be any one belonging to human immunoglobulins (hereinafter, referred to as hIg), and those of hIgG class are preferred. Further, any one of subclasses belonging to hIgG class such as hIgG1, hIgG2, hIgG3 or hIgG4 may be used. Further, the CL of the human chimeric antibody may be any one belonging to hIg, and those of κ class or λ class may be used.

Examples of the humanized antibody may include human type complementarity determining region (hereinafter, referred to as CDR)-grafted antibodies that are prepared by grafting an amino acid sequence of CDR of VH and VL of the antibody of the non-human animal to a proper region of VH and VL of the human antibody.

The CDR-grafted antibody may be produced by constructing cDNAs encoding V regions in which CDR sequences of VH and VL of the antibody of the non-human animal have been grafted to CDR sequences of VH and VL of any human antibody, constructing a CDR-grafted antibody expression vector by inserting them into an expression vector for host cells having genes encoding human antibody CH and human antibody CL, and expressing the human CDR-grafted antibody by introducing the expression vector into the host cells.

The CH of the human CDR-grafted antibody may be any one belonging to hIg. Those of hIgG class are preferred. Further, any one of subclasses belonging to hIgG class such as hIgG1, hIgG2, hIgG3 or hIgG4 may be used. Further, the CL of the CDR-grafted antibody may be any one belonging to hIg, and those of κ class or λ class may be used.

The human antibody, for example, may be obtained by isolating a human peripheral blood lymphocyte, infecting it with EB virus or the like to immortalize it, followed by cloning, culturing the lymphocyte capable of producing the antibody, and then purifying the antibody form the culture broth.

The human antibody may be prepared from the human antibody phage library. The human antibody phage library is a library in which antibody fragments such as Fab, scFv and the like are expressed on the phage surface by inserting an antibody gene prepared from human B cell into a phage gene. From the library, a phage expressing an antibody fragment having an antigen binding activity can be recovered, using its activity to bind to a solid-phased antigen as the marker. The antibody fragment can be further converted into a human antibody molecule composed of two complete H chains and two complete L chains.

The human antibody may be produced by obtaining cDNAs encoding VL and VH from a human antibody-producing hybridoma, inserting them into an expression vector for animal cell including DNAs encoding CL and CH of a human antibody in which one or more amino acid residues of the wild-type (hereinafter, referred to as WT) are substituted with Cys residues by the above described suitable method, and then introducing the vector into an animal cell to express the antibody.

The human antibody-producing hybridoma can be obtained from the human antibody-producing transgenic animal according to a hybridoma production method usually carried out in non-human mammals. The human antibody-producing transgenic animal is an animal in which a human antibody gene is introduced into cells. Specifically, the human antibody-producing transgenic mouse can be produced by introducing the human antibody gene into a mouse ES cell, transplanting the ES cell into an early stage embryo of a mouse and then generating it [Proc. Natl. Acad. Sci. USA, 97, 722 (2000)].

Alternatively, the human antibody may be produced by obtaining cDNAs encoding VL and VH from a human antibody-producing hybridoma, inserting them into an expression vector for animal cell including DNAs encoding CL and CH of a human antibody, substituting one or more amino acid residues of WT with Cys residues by the above described suitable method to construct a human antibody expression vector, and then introducing the human antibody expression vector into an animal cell to express the antibody.

The CH of WT used in the human antibody may be any one belonging to hIg. Those of hIgG class are preferred. Further, any one of subclasses belonging to hIgG class such as hIgG1, hIgG2, hIgG3 or hIgG4 may be used. Further, the CL of the human antibody may be any one belonging to hIg, and those of κ class or λ class may be used.

Specific examples of the antibodies produced by the method of the present invention may include, but not particularly limited to, the following antibodies.

Examples of the antibodies recognizing tumor-associated antigens may include anti-CD2 antibody [Anticancer Res., 13, 331 (1993)], anti-GD3 antibody [Cancer Immunol. Immunother., 36, 260 (1993)], anti-GM2 antibody [Cancer Res., 54, 1511 (1994)], anti-HER2 antibody [Proc. Natl. Acad. Sci. USA, 89, 4285 (1992), U.S. Pat. No. 5,725,856], anti-CD52 antibody [Proc. Natl. Acad. Sci. USA, 89, 4285 (1992)], anti-MAGE antibody [British J. Cancer, 83, 493 (2000)], anti-HM 1.24 antibody [Molecular Immunol., 36, 387 (1999)], anti-parathyroid hormone related peptide (PTHrP) antibody [Cancer, 88, 2909 (2000)], anti-bFGF antibody, anti-FGF-8 antibody [Proc. Natl. Acad. Sci. USA, 86, 9911 (1989)], anti-.bFGFR antibody, anti-FGF-8R antibody [J. Biol. Chem., 265, 16455 (1990)], anti-IGF antibody [J. Neurosci. Res., 40, 647 (1995)], anti-IGF-IR antibody [J. Neurosci. Res., 40, 647 (1995)], anti-PSMA antibody [J. Urology, 160, 2396 (1998)], anti-VEGF antibody [Cancer Res., 57, 4593 (1997)], anti-VEGFR antibody [Oncogene, 19, 2138 (2000), International Publication WO 96/30046], anti-CD20 antibody [Curr. Opin. Oncol., 10, 548 (1998), U.S. Pat. No. 5,736,137], anti-CD10 antibody, anti-EGFR antibody (International Publication WO 96/402010), anti-Apo-2R antibody (International Publication WO 98/51793), anti-ASCT2 antibody (International Publication WO 2001/008075), anti-CEA antibody [Cancer Res., 55 (23 suppl): 5935s-5945s, (1995)], anti-CD38 antibody, anti-CD33 antibody, anti-CD22 antibody, anti-EpCAM antibody, anti-A33 antibody and the like.

Examples of the antibodies recognizing allergy or inflammation-associated antigens may include anti-interleukin 6 antibody [Immunol. Rev., 127, 5 (1992)], anti-interleukin 6 receptor antibody [Molecular Immunol., 31, 371 (1994)], anti-interleukin 5 antibody [Immunol. Rev., 127, 5 (1992)], anti-interleukin 5 receptor antibody, anti-interleukin 4 antibody [Cytokine, 3, 562 (1991)], anti-interleukin 4 receptor antibody [J. Immunol. Methods, 217, 41 (1998)], anti-tumor necrosis factor antibody [Hybridoma, 13, 183 (1994)], anti-tumor necrosis factor receptor antibody [Molecular Pharmacol., 58, 237 (2000)], anti-CCR4 antibody [Nature, 400, 776 (1999)], anti-chemokine antibody (Peri et al., J. Immunol. Meth., 174, 249, 1994) or anti-chemokine receptor antibody [J. Exp. Med., 186, 1373 (1997)] and the like.

Examples of the antibodies recognizing cardiovascular disease-associated antigens may include anti-GPIIb/IIIa antibody [J. Immunol., 152, 2968 (1994)], anti-platelet-derived growth factor antibody [Science, 253, 1129 (1991)], anti-platelet-derived growth factor receptor antibody [J. Biol. Chem., 272, 17400 (1997)], anti-blood coagulation factor antibody [Circulation, 101, 1158 (2000)], anti-IgE antibody, anti-αVβ3 antibody, α4β7 antibody and the like.

Examples of the antibodies recognizing viral or bacterial infection-associated antigens may include anti-gp120 antibody [Structure, 8, 385 (2000)], anti-CD4 antibody [J. Rheumatology, 25, 2065 (1998)], anti-CCR5 antibody, anti-verotoxin antibody [J. Clin. Microbiol., 37, 396 (1999)] and the like.

Further, the present invention relates to a physiologically active substance produced by culturing cells using the aqueous solution which is prepared by the method for preparing the aqueous solution including the culture medium and the chelating agent, characterized by adding the chelating agent prior to the final pH adjustment of the aqueous solution.

Further, the present invention relates to a method for performing membrane filtration of the aqueous solution including the culture medium and the chelating agent, and a method for performing membrane filtration of the aqueous solution that is prepared by adding the chelating agent prior to the final pH adjustment of the aqueous solution.

As long as the membrane filtration method is a method of passing the aqueous solution for treatment through a porous membrane by pressure to remove components, particles, impurities or the like in the solution, the method is not particularly limited. The method is preferably microfiltration, ultrafiltration, dialysis, electrodialysis, or reverse osmosis, more preferably microfiltration, ultrafiltration or dialysis, and particularly preferably microfiltration.

A filtration membrane used in the membrane filtration includes, but is not particularly limited to, and preferably a microfiltration membrane, an ultrafiltration membrane, a dialysis membrane, an electrodialysis membrane, or a reverse osmosis membrane, more preferably a microfiltration membrane, an ultrafiltration membrane, a dialysis membrane, and particularly preferably a microfiltration membrane.

The material of the filtration membrane includes, but not particularly limited to, for example, cellulose acetate, aromatic polyamide, polyacrylonitrile, polyvinyl chloride, polyvinyl chloride-polyacrylonitrile copolymer, polysulfone, polyethersulfone (PES), polyvinylidene fluoride (PVDF), ceramics, polyvinyl alcohol, polyvinylidene difluoride, mixed ester of cellulose acetate and cellulose nitrate, polytetrafluoroethylene, alumina, styrene-divinylbenzen copolymer, TEFRON (registered trademark) or the like, and derivatives thereof or the like. Among them, polyethersulfone, polyvinylidene fluoride or the like are preferred.

Specific examples of the filtration membrane using polyethersulfone or the derivative thereof may include, for example, Millipore Express (registered trademark) PLUS Membrane Filters (pore size: 0.22 or 0.45 μm) (manufactured by Millipore), Millipore Express (registered trademark)SHC Cartridge Filters (manufactured by Millipore), Millipore Express (registered trademark)SHR Cartridge Filters (manufactured by Millipore), Supor (registered trademark) EBV (manufactured by Pall Corp.), Supor (registered trademark) EKV (manufactured by Pall Corp., catalog number: AB3EKV7PH4), Supor (registered trademark) EBV (manufactured by Pall Corp.), Supor (registered trademark) Life 200 (manufactured by Pall Corp.), Zarutopoa (registered trademark) 2 (membrane structure: two layers membrane, pore size: 2+0.1, 0.45+0.2 or 0.8+0.45 μm) (manufactured by sartorius stedim biotech), Zarutopoa (registered trademark) 2 XLG (membrane structure: two layers membrane, pore size: 0.8+0.2 μm) (manufactured by sartorius stedim biotech), Zarutopoa (registered trademark) 2 XLI (membrane structure: two layers membrane, pore size 0.35+0.2 μm) (manufactured by sartorius stedim biotech), Zarutopoa (registered trademark) 2 High Flow (manufactured by sartorius stedim biotech), PES Membrane Cartridge Filters TCS (pore size: 0.20 or 0.45 μm) (manufactured by ADVANTEC), or the like.

Specific examples of the filtration membrane using polyvinylidene fluoride or the derivative thereof may include, for example, Durapore (registered trademark) Membrane Filters (pore size: 0.10, 0.22, 0.45, 0.65 or 5.0 82 m) (manufactured by Millipore), Durapore (registered trademark) II Hydrophilic Filter Cartridge gV (manufactured by Millipore), Durapore (registered trademark) II Hydrophilic Filter Cartridge VV (manufactured by Millipore), Furorodain (registered trademark) II-DFLP (manufactured by Pall Corp.), Furorodain (registered trademark) II-DBLP (manufactured by Pall Corp.), Furorodain (registered trademark) II-DJLP (manufactured by Pall Corp.), Ultipor (registered trademark) VF-DV 20 (manufactured by Pall Corp.), Ultipor VF-DV 50 (manufactured by Pall Corp.), or the like.

Further, specific examples of the filtration membrane in combination with polyethersulfone or the derivative thereof and polyvinylidene fluoride or the derivative thereof may include, for example, Fluorodyne (registered trademark) Exgrade EDF Membrane Filter Cartridge (manufactured by Pall Corp., catalog number: AB3UEDF7PH4) or the like.

Furthermore, specific examples of the filtration membrane using membrane materials other than polyethersulfone or polyvinylidene fluoride may include, for example, Omnipore (registered trademark) Membrane Filters (pore size: 0.1, 0.2, 0.45, 1.0, 5.0 or 10 82 m) (manufactured by Millipore), MF-Millipore (registered trademark) Membrane Filters (pore size: 0.025, 0.05, 0.1, 0.22, 0.3, 0.45, 0.65, 0.8, 1.2, 3, 5 or 8 μm) (manufactured by Millipore), Nylon Membrane Filters (pore size: 0.20 or 5.0 μm) (manufactured by Millipore), Ultipor (registered trademark) N66 (pore size: 0.2 or 0.45 μm) (manufactured by Pall Corp.), Pojidain (registered trademark) (pore size: 0.10, 0.20, 0.3 or 0.45 μm) (manufactured by Pall Corp.), Varafine (registered trademark) VFSP (pore size: 0.2 or 0.45 μm) (manufactured by Pall Corp.), Varafine (registered trademark) VFSE (pore size: 0.02, 0.1 or 0.2 μm) (manufactured by Pall Corp.), Varafine (registered trademark) VFSG (pore size: 0.02, 0.1 or 0.2 μm) (manufactured by Pall Corp.), Zarutoron (manufactured by sartorius stedim biotech), Acetate Membrane Cartridge Filters TCR (pore size: 0.20, 0.45 or 8.0 μm) (manufactured by ADVANTEC), YUMICRON (registered trademark) Cartridge Filters (pore size: 0.2, 0.4, 0.6, 0.9 or 2.5 μm) (manufactured by Yuasa Membrane Systems Co., Ltd.), or the like.

The pore size of the filtration membrane is, but not particularly limited to, preferably from 1 nm to 100 μm, more preferably from 5 nm to 10 μm, more preferably from 10 nm to 1 μm, and particularly preferably from 0.1 μm to 0.5 μm. Specific example of the membrane pore size may be the pore size of the specific example of filtration membrane described above.

The filtration membrane may have a structure consisting of a single filtration membrane such as Millex (registered trademark) filter unit (manufactured by Millipore, catalog number: SLGV033RS), or a structure of two or more layers including one or more pre-filters such as 0.5/0.2 μm Express (registered trademark) SHC Disk W/Typar (manufactured by Millipore, catalog number: HGEP02550).

A method of evaluating filterability of the aqueous solution may include, but is not particularly limited to, for example, a Vmax test or the like. Vmax (L/m$^2$) is the maximum processing amount per unit membrane area, which can be obtained after infinite time from the start of filtration, and can be measured by the method described in BioPharm, 46, September (1995).

Further, the present invention relates to a method for improving membrane filterability of the aqueous solution in which the aqueous solution including the chelating agent is prepared by adding the chelating agent to the aqueous solution to perform membrane filtration of the aqueous solution. Also, the present invention relates to a method for improving membrane filterability of the aqueous solution in which the aqueous solution including the chelating agent and the culture medium is prepared by adding the chelating agent and the culture medium to the aqueous solution to perform membrane filtration of the aqueous solution.

Furthermore, the present invention relates to a method for producing a physiologically active substance by preparing the aqueous solution including the culture medium and the chelating agent by adding the chelating agent to the aqueous solution prior to the final pH adjustment of the aqueous solution, performing membrane filtration of the aqueous solution, and then culturing cells using the resulting aqueous solution.

EXAMPLES

Hereinafter, the present invention will be described in more detail with reference to the following Examples. However, these Examples are for illustrative purposes only, and the invention is not intended to be limited by these Examples, Example 1

Effect of Chelating Agent on Filterability Improvement

The effects of various chelating agents on filterability of an aqueous solution when added during the preparation of the aqueous solution including a powder culture medium were examined to demonstrate improvement of Vmax (maximum processing amount per unit membrane area) value.

Preparation of the aqueous solution was carried out by the following procedure. First, each 2.0 g of trisodium citrate dihydrate (manufactured by Kozakai Pharmaceutical Co.), L-malic acid (manufactured by Wako, catalog number: 138-07512), or ethylenediaminetetraacetic acid iron(III) sodium salt (hereinafter, referred to as EDTA iron(III) sodium salt) (manufactured by Sigma-Aldrich, catalog number: EDFS-100G) was added as a chelating agent to 900 mL of pure water (hereinafter, referred to as PW), followed by stirring. Each pH after completely dissolving the chelating agent was 8.41 for trisodium citrate dihydrate added solution, 2.57 for L-malic acid added solution, and 5.11 for EDTA iron(III) sodium salt added solution.

Next, 6.7 g of SOY HYDROLYSATE UF (manufactured by SAFC Bioscience, catalog number: 91052-1K3986) was added, followed by stirring for about 15 minutes. 22.6 g of improved powder culture medium EX-CELL 302 (manufactured by SAFC Bioscience) containing amino acids, metal salts, and vitamins and 0.5 mL of 1 mmol/L methotrexate solution (manufactured by Sigma Aldrich, catalog number: M8407-500MG) dissolved in PBS (manufactured by Invitrogen, catalog number: 14190-250) were added, followed by stirring for about 30 minutes.

In addition, 1.6 g of sodium bicarbonate (manufactured by Kanto Chemical Co., Inc., catalog number: 37116-00) was added for the final pH adjustment. After stirring for about 5 minutes, the volume was adjusted to 1 L with PW, followed by stirring for about 10 minutes.

Each concentration of the added chelating agents described above after the preparation of the aqueous solution was 6.8 mmol/L for trisodium citrate dihydrate, 15 mmol/L for L-malic acid, and 5.4 mmol/L for EDTA iron(III) sodium salt.

Next, Vmax test of the prepared aqueous solution was performed as follows. 1 L of the test aqueous solution was placed in a pressurized tank (manufactured by Millipore). Millex (registered trademark) GV Filter Unit (manufactured by Millipore, catalog number: SLGV033RS) with a pore size of 0.22 μm was used as the test filter. The filter was connected to the tank, and 100 kPa of pressure was applied by the compressed air.

The valve on the tank was slightly opened before starting the test, and the filter was wet with the aqueous solution. After wetting the filter, the testing was started by fully opening the valve. The time point of fully opening the valve was set to 0, and the time taken to increase 5 g of the filtration processing amount was measured. The density of the aqueous solution was considered as 1 g/mL, and the filtration amount (V) was calculated from the measured weight. The measurement was carried out for more than three minutes. A graph was made by plotting the measurement values with the time (t) on the horizontal axis and t/V on the vertical axis to calculate Vmax from the reciprocal of the slope of the obtained straight line.

The results are shown in FIG. 1. Vmax (L/m$^2$) value was 452 for the aqueous solution to which no chelating agent was added, but increased to 1931 for the aqueous solution to which trisodium citrate dihydrate was added as the chelating agent, 2483 for the aqueous solution to which L-malic acid was added as the chelating agent, and 1834 for the aqueous solution to which EDTA iron(III) sodium salt was added as the chelating agent.

These results showed that Vmax value of the aqueous solution can be increased by addition of the chelating agent during preparation of the aqueous solution.

Example 2

Timing of Addition and Filterability-Improving Effect of Trisodium Citrate Dehydrate Timing of addition and filterability-improving effect of trisodium citrate dehydrate during preparation of the aqueous solution including a powder culture medium were examined to demonstrate that Vmax (maximum processing amount per unit membrane area) can be greatly increased by addition of trisodium citrate dihydrate together with or prior to the powder culture medium containing amino acids, metal salts, vitamins or the like. It was also demonstrated that Vmax (maximum processing amount per unit membrane area) can be increased by addition of the trisodium citrate dihydrate prior to the final pH adjustment.

Preparation of the aqueous solution was carried out by the following procedure, except the addition of trisodium citrate dihydrate. First, 6.7 g of SOY HYDROLYSATE UF (manufactured by SAFC Bioscience, catalog number: 91052-

5K3986) was added to 900 mL of pure water (hereinafter, referred to as PW), followed by stirring for about 15 minutes.

22.6 g of improved EX-CELL 302 (manufactured by SAFC Bioscience) containing amino acids, metal salts, and vitamins and 0.5 mL of 1 mmol/L methotrexate solution (manufactured by Sigma Aldrich, catalog number: M8407-500MG) dissolved in PBS (manufactured by Invitrogen, catalog number: 14190-250) were added, followed by stirring for about 30 minutes.

In addition, 1.6 g of sodium bicarbonate (manufactured by Kanto Chemical Co., Inc., catalog number: 37116-00) was added for the final pH adjustment. After stirring for about 5 minutes, the volume was adjusted to 1 L with PW, and the mixture was further stirred for about 10 minutes.

During the procedure of preparing the aqueous solution, trisodium citrate dihydrate (manufactured by Kozakai Pharmaceutical Co.) was added at the time points of the following conditions A to H to prepare aqueous solutions. The concentration of the added trisodium citrate dihydrate after preparation of the aqueous solution described above was 0.1 g/L (0.34 mmol/L).

Condition A: no addition
Condition B: 10 minutes before addition of SOY HYDROLYSATE UF
Condition C: 1 minute before addition of SOY HYDROLYSATE UF
Condition D: concurrent addition of SOY HYDROLYSATE UF
Condition E: 10 minutes before addition of improved EX-CELL 302
Condition F: concurrent addition of improved EX-CELL 302
Condition G: 15 minutes before addition of sodium bicarbonate
Condition H: immediately after preparation of 1 L solution with PW Next, Vmax test of the prepared aqueous solution was performed as follows. 1 L of the test aqueous solution was placed in a pressurized tank (manufactured by Millipore). Millex (registered trademark) GV Filter Unit (manufactured by Millipore, catalog number: SLGV033RS) with a pore size of 0.22 μm was used as the test filter. The filter was connected to the tank, and 100 kPa of pressure was applied by the compressed air. The valve on the tank was slightly opened before starting the test, and the filter was wet with the aqueous solution. After wetting the filter, the testing was started by fully opening the valve.

The time point of fully opening the valve was set to 0, and the time taken to increase 5 g of the filtration processing amount was measured. The density of the aqueous solution was considered as 1 g/mL, and the filtration amount (V) was calculated from the measured weight. The measurement was carried out for more than three minutes. A graph was made by plotting the measurement values with the time (t) on the horizontal axis and t/V on the vertical axis to calculate Vmax from the reciprocal of the slope of the obtained straight line.

Figure 2:
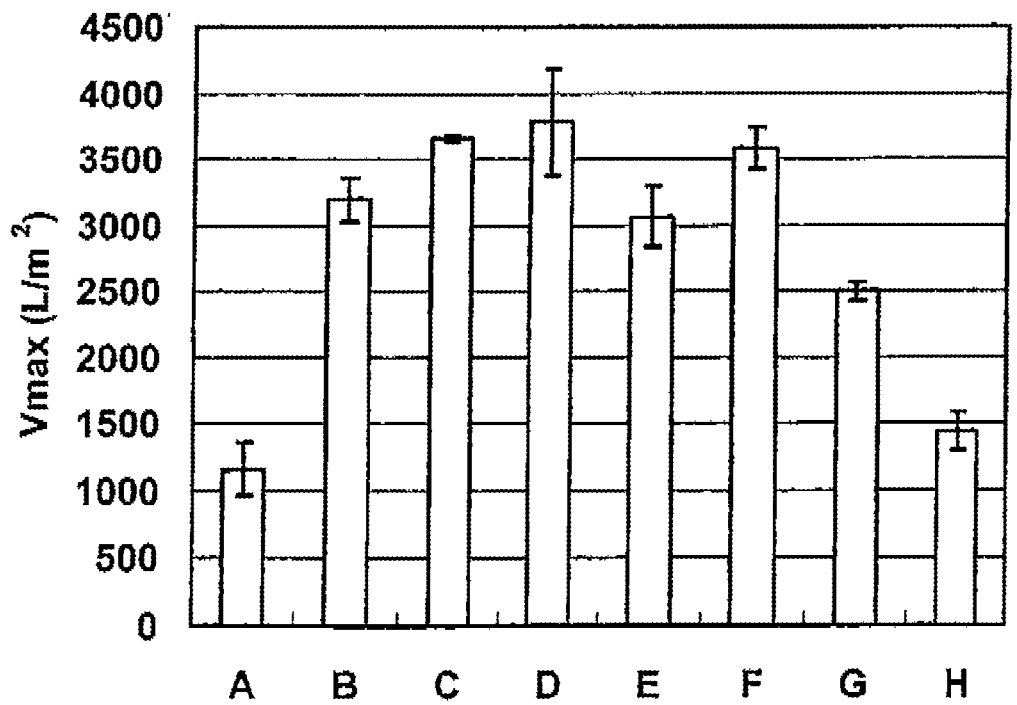
FIG. 2 shows that filterability of the aqueous solution is remarkably improved by adding the chelating agent prior to the final pH adjustment of the aqueous solution, in which the vertical axis represents the maximum processing amount per unit membrane area [Vmax ($L/m^2$)], and the horizontal axis represents the time point of adding the chelating agent.

The results are shown in FIG. 2. Vmax (L/m$^2$) value was 1163 under Condition A, 3199 under Condition B, 3652 under Condition C, 3783 under Condition D, 3060 under Condition E, and 3581 under Condition F, indicating that filterability of the aqueous solution can be greatly improved by addition of trisodium citrate dihydrate together with or prior to the improved EX-CELL 302.

Furthermore, Vmax (L/m$^2$) value was 2502 under Condition G, indicating that filterability of the aqueous solution can be improved by addition of trisodium citrate dihydrate prior to addition of sodium bicarbonate as a pH adjustment process. Meanwhile, Vmax value was 1441 under Condition H of adding trisodium citrate dihydrate after pH adjustment, indicating that filterability improvement of the aqueous solution is equivalent to or slightly higher than that under Condition A.

These results showed that Vmax (maximum processing amount per unit membrane area) of the aqueous solution can be increased by addition of trisodium citrate dihydrate prior to the final pH adjustment tank process. Further, particularly, Vmax can be increased by addition of trisodium citrate dihydrate together with or prior to the powder culture medium containing amino acids, metal salts, vitamins or the like.

Example 3

Correlation between Concentration of Added Trisodium Citrate Dihydrate and Filterability of Aqueous Solution Correlation between filterability and concentration of trisodium citrate dihydrate added during preparation of the aqueous solution was examined to demonstrate that Vmax (maximum processing amount per unit membrane area) increased in a concentration-dependent manner.

Preparation of the aqueous solution was carried out by the following procedure. First, 0 g (no addition), 0.1 g or 1.0 g of trisodium citrate dihydrate (manufactured by Kozakai Pharmaceutical Co.) was added to 900 mL of pure water (hereinafter, referred to as PW), and stirred. After completely dissolving trisodium citrate dihydrate, 6.7 g of SOY HYDROLYSATE UF (manufactured by SAFC Bioscience, catalog number: 91052-1K3986) was added, followed by stirring for about 15 minutes.

22.6 g of improved EX-CELL 302 (manufactured by SAFC Bioscience) containing amino acids, metal salts, vitamins, and the like and 0.5 mL of 1 mmol/L methotrexate solution (manufactured by Sigma Aldrich, catalog number: M8407-500MG) dissolved in PBS (manufactured by Invitrogen, catalog number: 14190-250) were added, followed by stirring for about 30 minutes.

In addition, 1.6 g of sodium bicarbonate (manufactured by Kanto Chemical Co., Inc., catalog number: 37116-00) was added for the final pH adjustment. After stirring for about 5 minutes, the volume was adjusted to 1 L with PW, followed by stirring for about 10 minutes. The concentration of added trisodium citrate dihydrate described above after preparation of the aqueous solution was 0 g/L (no addition), 0.1 g/L (0.34 mmol/L), or 1.0 g/L (3.4 mmol/L).

Next, Vmax test of the prepared aqueous solution was performed as follows. 1 L of the test aqueous solution was placed in a pressurized tank (manufactured by Millipore). Millex (registered trademark) GV Filter Unit (manufactured by Millipore, catalog number: SLGV033RS) with a pore size of 0.22 μm was used as the test filter. The filter was connected to the tank, and 100 kPa of pressure was applied by the compressed air.

The valve on the tank was slightly opened before starting the test, and the filter was wet with the aqueous solution. After wetting the filter, the testing was started by fully opening the valve. The time point of fully opening the valve was set to 0, and the time taken to increase 5 g of the filtration processing amount was measured. The density of the aqueous solution was considered as 1 g/mL, and the filtration amount (V) was calculated from the measured weight. The measurement was carried out for more than three minutes. A graph was made by plotting the measurement values with the time (t) on the horizontal axis and t/V on the vertical axis to calculate Vmax from the reciprocal of the slope of the obtained straight line.

Figure 3:
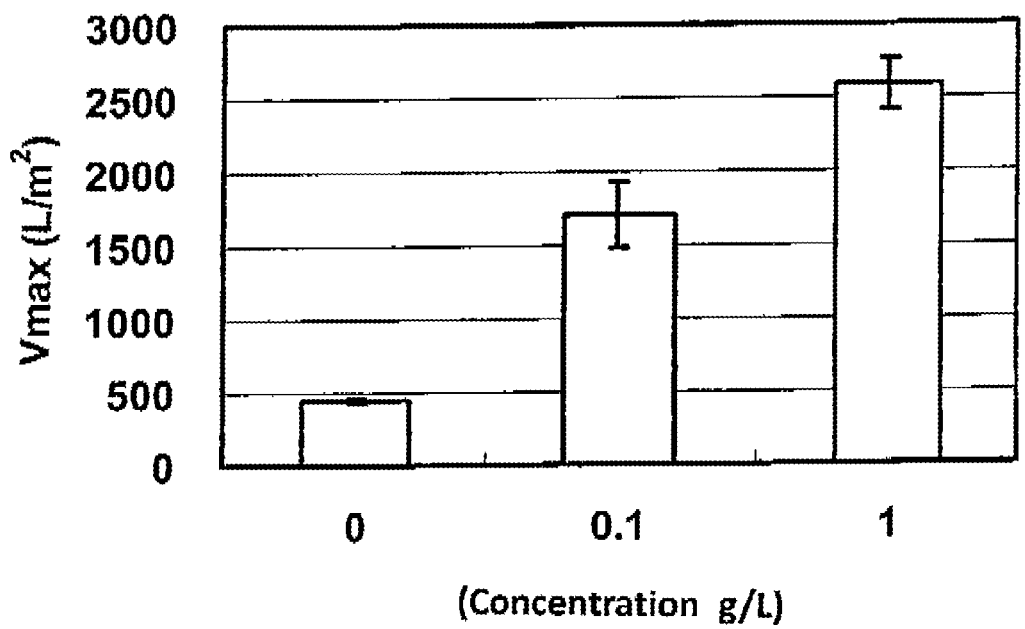
FIG. 3 shows that the chelating agent improves filterability in a concentration-dependent manner, in which the vertical axis represents the maximum processing amount per unit membrane area [Vmax ($L/m^2$)], and the horizontal axis represents the concentration (g/L) of the chelating agent.

The results are shown in FIG. 3. Vmax (L/m$^2$) value was 452 for the aqueous solution to which no chelating agent was added, but increased to 1706 for the aqueous solution to which 0.1 g/L of trisodium citrate dehydrate was added, and 2588 for the aqueous solution to which 0.1 g/L of trisodium citrate dehydrate was added.

These results showed that Vmax value of the aqueous solution can be increased depending the concentration of trisodium citrate dihydrate by addition of trisodium citrate dihydrate as the chelating agent prior to the final pH adjustment of the aqueous solution.

Example 4

Membrane Material/Membrane Structure-Independent Filterability-Improving Effect of Chelating Agent In the preparation of the aqueous solution containing the powder culture medium, the filterability-improving effects of the chelating agents were examined by using a plurality of filtration membranes. As a result, it was revealed that Vmax (maximum processing amount per unit membrane area) value can be improved by a polyvinylidene fluoride (hereinafter, referred to as PVDF) membrane with a pore size of 0.22 μm, or by a PES membrane with a pore size of 0.2 μm (hereinafter, referred to as PES membrane of 0.5/0.2 μm pore size) in combination with polyethersulfone (hereinafter, referred to as PES) membranes with a pore size of 0.5 82 m as a pre-filter.

Preparation of the aqueous solution was carried out by the following procedure. First, 0 g (no addition) or 0.1 g of trisodium citrate dihydrate (manufactured by Kozakai Pharmaceutical Co.) was added to 900 mL of pure water (hereinafter, referred to as PW), and stirred. After completely dissolving trisodium citrate dihydrate, 6.7 g of SOY HYDROLYSATE UF (manufactured by SAFC Bioscience, catalog number: 91052-1K3986 or 91052-5K3986) was added, followed by stirring for about 15 minutes.

22.6 g of improved powder culture medium EX-CELL 302 (manufactured by SAFC Bioscience) containing amino acids, metal salts, vitamins and the like, and 0.5 mL of 1 mmol/L methotrexate solution (manufactured by Sigma Aldrich, catalog number: M8407-500MG) dissolved in PBS (manufactured by Invitrogen, catalog number: 14190-250) were added, followed by stirring for about 30 minutes. In addition, 1.6 g of sodium bicarbonate (manufactured by Kanto Chemical Co., Inc., catalog number: 37116-00) was added for the final pH adjustment. After stirring for about 5 minutes, the volume was adjusted to 1 L with PW, followed by further stirring for about 10 minutes. The concentration of the added trisodium citrate dehydrate described above after preparation of the aqueous solution was 0 g/L (no addition) or 0.1 g/L (0.34 mmol/L).

Next, Vmax test of the prepared aqueous solution was performed by the following procedure using the PVDF membrane, Millex (registered trademark) GV Filter Unit (manufactured by Millipore, catalog number: SLGV033RS) with a pore size of 0.22 μm as the test filter. 1 L of the test aqueous solution was placed in a pressurized tank (manufactured by Millipore). The filter was connected to the tank, and 100 kPa of pressure was applied by the compressed air.

The valve on the tank was slightly opened before starting the test, and the filter was wet with the aqueous solution. After wetting the filter, the testing was started by fully opening the valve. The time point of fully opening the valve was set to 0, and the time taken to increase 5 g of the filtration processing amount was measured. The density of the aqueous solution was considered as 1 g/mL, and the filtration amount (V) was calculated from the measured weight. The measurement was carried out for more than three minutes. A graph was made by plotting the measurement values with the time (t) on the horizontal axis and t/V on the vertical axis to calculate Vmax from the reciprocal of the slope of the obtained straight line.

In addition, Vmax test of the prepared aqueous solution was performed by the following procedure using 0.5/0.2 μm Expres SHCC Disk W/Typar (manufactured by Millipore, catalog number: HGEP02550) which is a PES membrane with a pore size of 0.5/0.2 μm as the test filter. 1 L of the test aqueous solution was placed in a pressurized tank (manufactured by Millipore).

The test filter sufficiently wetted by PW was attached to a folder (manufactured by Millipore), and the folder was connected to a pressure tank. Air was fully extruded from the air vent by opening the valve included in the folder. After applying 120 kPa of pressure by the compressed air in the pressure tank, the test was started by fully opening the valve.

The time point of fully opening the valve was set to 0, and the time taken to increase 5 g of the filtration processing amount was measured. The density of the aqueous solution was considered as 1 g/mL, and the filtration amount (V) was calculated from the measured weight. The measurement was carried out for more than three minutes. A graph was made by plotting the measurement values with the time (t) on the horizontal axis and t/V on the vertical axis to calculate Vmax from the reciprocal of the slope of the obtained straight line.

Figure 4:
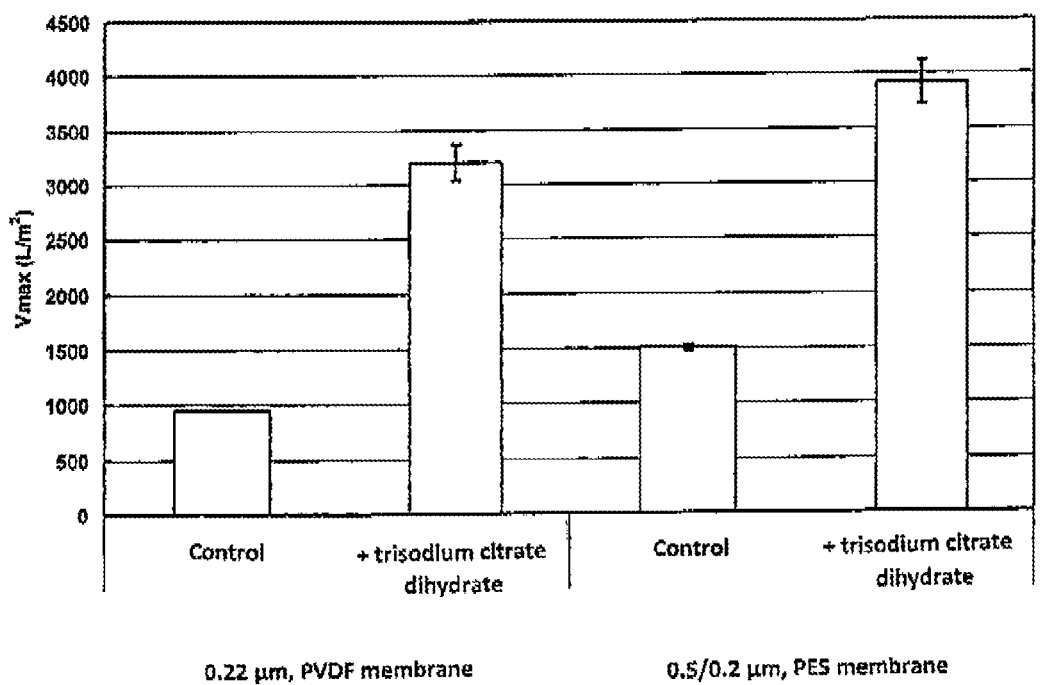
FIG. 4 shows that filterability-improving effect of the chelating agent does not depend on membrane materials and membrane structures, in which the vertical axis represents the maximum processing amount per unit membrane area [Vmax ($L/m^2$)], and the horizontal axis represents the material of the filtration membrane.

The results are shown in FIG. 4. With respect to filtration using the PVDF membrane with a pore size of 0.22 μm, Vmax (L/m$^2$) value was 957 for the aqueous solution to which no trisodium citrate dehydrate was added, but increased to 3199 for the aqueous solution to which trisodium citrate dehydrate was added. Further, with respect to filtration using the PES membrane with a pore size of 0.5/0.2 μm, Vmax (L/m$^2$) value was 1511 for the aqueous solution to which no trisodium citrate dehydrate was added, but increased to 3922 for the aqueous solution to which trisodium citrate dehydrate was added.

These results showed that filterability of the aqueous solution can be improved by addition of the chelating agent to the aqueous solution prior to the final pH adjustment of the aqueous solution, irrespective of the membrane material to be used such as PVDF or PES. It was also revealed that filterability of the aqueous solution can be improved by addition of the chelating agent prior to the final pH adjustment of the aqueous solution, irrespective of the membrane structure to be used such as a single layer or a plurality of layers prepared in combination with the pre-filter.

Example 5

Animal Cell Culture and Physiologically Active Substance Production Using Aqueous Solution Prepared by Addition of Chelating Agent Prior to Final pH Adjustment Animal cell culture was performed using the aqueous solution which is prepared by addition of trisodium citrate dihydrate prior to the final pH adjustment. As a result, in the aqueous solution to which trisodium citrate dihydrate was added, cell growth and titers were equivalent to or greater than those in the aqueous solution to which no trisodium citrate dihydrate was added.

The preparation procedure of 1 L production aqueous solution will be described as follows.

First, 0 g (no addition) or 0.1 g of trisodium citrate dihydrate (manufactured by Kozakai Pharmaceutical Co.) was added to about 900 mL of pure water (hereinafter, referred to as PW), and stirred. After completely dissolving trisodium citrate dihydrate, 6.7 g of SOY HYDROLYSATE UF (manufactured by SAFC Bioscience, catalog number: 91052-1K3986 or 91052-5K3986) was added, followed by stirring for about 15 minutes.

Next, 22.6 g of improved powder culture medium EX-CELL 302 (manufactured by SAFC Bioscience) containing amino acids, metal salts, vitamins and the like, and 0.5 mL of 1 mmol/L methotrexate solution (manufactured by Sigma Aldrich, catalog number: M8407-500MG) dissolved in PBS (manufactured by Invitrogen, catalog number 14190-250) were added, followed by stirring for about 30 minutes.

In addition, 1.6 g of sodium bicarbonate (manufactured by Kanto Chemical Co., Inc., catalog number: 37116-00) was added for the final pH adjustment. After stirring for about 5 minutes, the volume was adjusted to 1 L with PW, followed by stirring for about 10 minutes to prepare the production aqueous solution. The concentration of the added trisodium citrate dehydrate described above after preparation of the aqueous solution was 0 g/L (no addition) or 0.1 g/L (0.34 mmol/L), Monoclonal antibody-expressing CHO cells were fed-batch cultured using the production aqueous solution prepared by the above procedure in a 3 L-reactor for 14 days. The seeding density at the initial stage of culture was about $3.0 \times 10^6$ cells/mL, and the temperature and pH of the aqueous solution for culture during the culture period were controlled to be 35° C. and 7.10, respectively.

The feeding aqueous solution consists of amino acids [L-alanine, L-arginine monohydrochloride, L-asparagine monohydrate, L-cystine dihydrochloride, L-glutamic acid, L-histidine monohydrochloride dihydrate, L-isoleucine, L-leucine, L-lysine monohydrochloride, L-phenylalanine, L-proline, L-serine, L-threonine, L-tryptophan, L-tyrosine disodium salt, L-valine (all manufactured by Sigma. Aldrich), L-aspartic acid, glycine (all manufactured by Wako Pure Chemical Industries, Ltd.), L-alanyl-L-glutamine (manufactured by Kyowa Hakko Bio Co., Ltd.) and L-methionine (manufactured by Junsei Chemical Co.)], vitamins [D-biotin, D-calcium pantothenate, choline chloride, folic acid, myo-inositol, niacinamide, pyridoxal hydrochloride, riboflavin, thiamine hydrochloride, cyanocobalamin (all manufactured by Sigma Aldrich)], recombinant human insulin (manufactured by JRH Bioscience), ethanolamine (manufactured by Sigma Aldrich), SOY HYDROLYSATE UF (manufactured by SAFC Bioscience), cholesterol lipid concentrate solution (250× aqueous solution, manufactured by Invitrogen), ethylenediaminetetraacetic acid iron(II) sodium salt (manufactured by Sigma Aldrich) and glucose (manufactured by Wako Pure Chemical Industries, Ltd.). The feeding aqueous solution was added in an amount of about 6.3% of the initial production aqueous solution on day 3, 6, 9 and 12 after culture.

As a result, in the culture using the aqueous solution to which no trisodium citrate dehydrate was added, the maximum viable cell density reached $5.4 \times 10^6$ cells/mL and the titer of the monoclonal antibody at the end of the culture was 1.8 g/L, whereas in the culture using the aqueous solution to which 0.1 g/L of trisodium citrate dehydrate was added, the maximum viable cell density reached $5.8 \times 10^6$ cells/mL and the titer of the monoclonal antibody at the end of the culture was 1.9 g/L.

These results indicate that in the aqueous solution prepared by adding trisodium citrate dihydrate prior to the final pH adjustment, cell growth and titers were equivalent to or greater than those in the aqueous solution prepared without addition of trisodium citrate dihydrate.

Example 6

Filterability-Improving Effect by Addition of N-acetylneuraminic acid dehydrate

The effect of addition of N-acetylneuraminic acid dihydrate as the chelating agent during preparation of the aqueous solution containing a powder culture medium on the filterability of the aqueous solution was examined to demonstrate that Vmax (maximum processing amount per unit membrane area) of the aqueous solution can be improved.

Preparation of the aqueous solution was carried out by the following procedure. First, 4.0 g of sodium hydroxide (manufactured by Junsei Chemical Co., catalog number: 39155-0301), 4.5 g of L-tyrosine disodium salt (manufactured by SIGMA, catalog number: T1145-1000), and 6.16 g of L-(−)-Cystine dihydrochloride (manufactured by Wako Pure Chemical Industries, Ltd. catalog number: 034-05322) were added to 160 mL of pure water (hereinafter, abbreviated as PW), followed by stirring for about 30 minutes, and the volume was adjusted to 200 mL with PW to prepare the aqueous solution (hereinafter, abbreviated as Cys-Tyr solution).

Next, 32.6 g of a powder culture medium, Efficient Feed A containing amino acids, metal salts, vitamins, and the like (manufactured by Life Technologies, catalog number: A12870SB), 0.5 mL of a liquid additive polyamine solution (manufactured by Life Technologies, catalog number: A12872SA), 27.1 g of a powder culture medium, Efficient Feed B containing amino acids, metal salts, vitamins, and the like (manufactured by Life Technologies, catalog number: A11498SA), 5.0 g of L(+)-glutamine (manufactured by Wako Pure Chemical Industries, Ltd. catalog number: 078-00525), 30.0 g of peptone SE50MAF-UF (manufactured by Wako Pure Chemical Industries, Ltd. catalog number: P42474), and 70.0 g of D(+)-glucose (manufactured by Wako Pure Chemical Industries, Ltd. catalog number: 041-00595), and 30.9 g of N-acetylneuraminic acid dihydrate (manufactured by Kyowahakko Bio Co., Ltd.) as the chelating agent were added to 800 mL of PW, followed by stirring for about 30 minutes.

The pH after stirring was 4.05. Then, 50 mL of Cys-Tyr solution was added, followed by stirring for about 20 minutes. The pH after addition of Cys-Tyr solution was 4.37. Thereafter, 17 mL of 5 mol/l sodium hydroxide solution (manufactured by Wako Pure Chemical Industries, Ltd., catalog number: 196-05375) was added for the final pH adjustment, followed by stirring for about 20 minutes, then the volume was adjusted to 1 L with PW to prepare Solution A. The final pH of Solution A was 8.1. The concentration of the added N-acetylneuraminic acid dehydrate described above after preparation of the aqueous solution was 30.9 g/L (89 mmol/L).

Meanwhile, to 800 mL of PW, 32.6 g of a powder culture medium, Efficient Feed A containing amino acids, metal salts, vitamins, and the like (manufactured by Life Technologies, catalog number: A12870SB), 0.5 mL of a liquid additive polyamine solution (manufactured by Life Technologies, catalog number: A12872SA), 27.1 g of a powder culture medium, Efficient Feed B containing amino acids, metal salts, vitamins, and the like (manufactured by Life Technologies, catalog number: A11498SA), 5.0 g of L-(+)-glutamine (manufactured by Wako Pure Chemical Industries, Ltd. catalog number: 078-00525), 30.0 g of peptone SE50MAF-UF (manufactured by Wako Pure Chemical Industries, Ltd. catalog number: P42474), and 70.0 g of D(+)-glucose (manufactured by Wako Pure Chemical Industries, Ltd. catalog number: 041-00595) were added, and 28 mL of 5 mol/l hydrochloric acid (manufactured by Wako Pure Chemical Industries, Ltd., Cat: 081-05435) was added as not a chelating agent as but an acid, followed by stirring for about 30 minutes. The pH after stirring was 3.09. Then, 50 mL of Cys-Tyr solution was added, followed by stirring for about 20 minutes. The pH after addition of Cys-Tyr solution was 3.39.

Thereafter, 28 mL of 5 mol/l sodium hydroxide solution (manufactured by Wako Pure Chemical Industries, Ltd., catalog number: 196-05375) was added for the final pH adjustment, followed by stirring for about 20 minutes, then the volume was adjusted to 1 L with PW to prepare Solution B. The final pH of Solution B was 8.1.

Next, Vmax test of the prepared aqueous solution was performed by the following procedure. 1 L of the test aqueous solution was placed in a pressurized tank (manufactured by Millipore). Millex (registered trademark) GV Filter Unit (manufactured by Millipore, catalog number: SLGV033RS) with a pore size of 0.22 μm was used as the test filter.

The filter was connected to the tank, and 100 kPa of pressure was applied by the compressed air. The valve on the tank was slightly opened before starting the test, and the filter was wet with the aqueous solution. After wetting the filter, the testing was started by fully opening the valve.

The time point of fully opening the valve was set to 0, and the time taken to increase 5 g of the filtration processing amount was measured. The density of the aqueous solution was considered as 1 g/mL, and the filtration amount (V) was calculated from the measured weight. The measurement was carried out for more than three minutes. A graph was made by plotting the measurement values with the time (t) on the horizontal axis and t/V on the vertical axis to calculate Vmax from the reciprocal of the slope of the obtained straight line.

Figure 5:
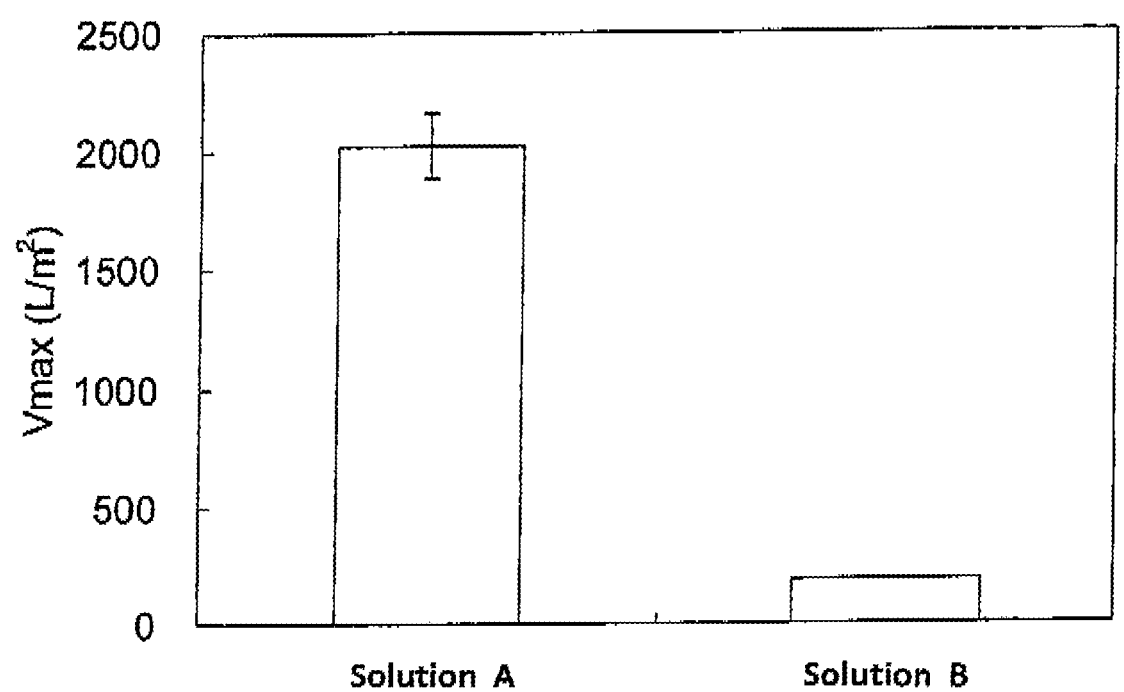
FIG. 5 shows that filterability of the aqueous solution is remarkably improved by adding sialic acid as the chelating agent, in which the vertical axis represents the maximum processing amount per unit membrane area [Vmax ($L/m^2$)], and the horizontal axis represents the kind of the solution.

The results are shown in FIG. 5, Vmax (L/m$^2$) value was 190 for Solution B to which no chelating agent was added, but increased to 2025 for Solution A to which N-acetylneuraminic acid dihydrate was added as the chelating agent.

These results showed that Vmax value of the aqueous solution can be increased by addition of N-acetylneuraminic acid dihydrate as the chelating agent during preparation of the aqueous solution containing the powder culture medium.

Although the present invention has been described in detail with reference to specific embodiments, it will be apparent to those skilled in the art that various modifications and changes may be made thereto without departing from the spirit and scope of the present invention. Further, the present application is based on Japanese Patent Application No. 2010-290444, filed on Dec. 27, 2010, the disclosure of which is hereby incorporated by reference in its entirety.

INDUSTRIAL APPLICABILITY

The present invention provides a method for preparing an aqueous solution having remarkably improved filterability. A highly versatile aqueous solution for cell culture which can be stably membrane-filtered in a short time is provided by using the preparation method. Also, provided are an aqueous solution having remarkably improved filterability which is prepared by the preparation method, a method for culturing cells using the aqueous solution which is prepared by the preparation method, a method for producing a physiologically active substance using the culturing method, a physiologically active substance produced by the method for producing the physiologically active substance, a method for performing membrane filtration of the aqueous solution which is prepared by the preparation method, a method for improving membrane filterability of the aqueous solution, characterized in that the aqueous solution is prepared by addition of a chelating agent, or a method for producing the physiologically active substance by preparing the aqueous solution, performing membrane filtration of the aqueous solution, and then culturing cells using the aqueous solution.

The invention claimed is:

1. A method for preparing an aqueous solution comprising a powdered culture medium and a chelating agent, comprising adding the chelating agent to water prior to the final pH adjustment of the aqueous solution,
    wherein the powdered culture medium is a culture medium for animal cells,
    the chelating agent is added before addition of the powdered culture medium or simultaneously together with the powdered culture medium, and
    a concentration of the chelating agent is 0.1 to 100 mmol/L.

2. The method for preparing an aqueous solution according to claim 1, wherein the powdered culture medium is a culture medium for Chinese hamster ovary tissue-derived CHO cells.

3. The method for preparing an aqueous solution according to claim 1, wherein the chelating agent is one or more selected from citric acid, malic acid, ethylenediaminetetraacetic acid, ethylenediaminetetraacetic acid iron(III) sodium salt, sialic acid, and salts or hydrates thereof.

4. A method for culturing cells comprising culturing the cells in an aqueous solution comprising a powdered culture medium and a chelating agent,
    wherein the aqueous solution is prepared by adding the chelating agent to water prior to the final pH adjustment of the aqueous solution,
    the cells are animal cells,
    the chelating agent is added before addition of the powdered culture medium or simultaneously together with the powdered culture medium, and
    a concentration of the chelating agent is 0.1 to 100 mmol/L.

5. The method for culturing cells according to claim 4, wherein the animal cells are Chinese hamster ovary tissue-derived CHO cells.

6. The method for culturing cells according to claim 4, wherein the chelating agent is one or more selected from citric acid, malic acid, ethylenediaminetetraacetic acid, ethylenediaminetetraacetic acid iron(III) sodium salt, sialic acid, and salts or hydrates thereof.

7. A method for producing a physiologically active substance comprising culturing cells in an aqueous solution to produce the physiologically active substance and isolating the physiologically active substance,
    wherein the aqueous solution comprises a powdered culture medium and a chelating agent and is prepared by adding the chelating agent to water prior to the final pH adjustment of the aqueous solution, the physiologically active substance is a peptide or a protein, the chelating agent is added before addition of the powdered culture medium or simultaneously together with the powdered culture medium, and a concentration of the chelating agent is 0.1 to 100 mmol/L.

8. The method for producing a physiologically active substance according to claim 7, wherein the protein is a glycoprotein or an antibody.

9. The method for producing a physiologically active substance according to claim 7, wherein the chelating agent is one or more selected from citric acid, malic acid, ethylenediaminetetraacetic acid, ethylenediaminetetraacetic acid iron(III) sodium salt, sialic acid, and salts or hydrates thereof.

10. A method for performing membrane-filtration of an aqueous solution comprising a powdered culture medium and a chelating agent, said method comprising performing membrane-filtration of the aqueous solution, wherein the aqueous solution is prepared by adding a chelating agent prior to the final pH adjustment of the aqueous solution, the chelating agent is added before addition of the powdered culture medium or simultaneously together with the powdered culture medium, and a concentration of the chelating agent is 0.1 to 100 mmol/L.

11. The method for performing membrane-filtration according to claim 10, wherein the chelating agent is one or more selected from citric acid, malic acid, ethylenediaminetetraacetic acid, ethylenediaminetetraacetic acid iron (III) sodium salt, sialic acid, and salts or hydrates thereof.

12. The method for performing membrane-filtration according to claim 10, wherein the powdered culture medium further includes one or more selected from metal salts, sugars, and vitamins.

13. The method for performing membrane-filtration according to claim 10, wherein the powdered culture medium is a culture medium for cell culture.

14. The method for performing membrane-filtration according to claim 13, wherein the powdered culture medium is a culture medium for animal cells.

15. The method for performing membrane-filtration according to claim 14, wherein the powdered culture medium is a culture medium for Chinese hamster ovary tissue-derived CHO cells.

16. The method for performing membrane-filtration according to claim 10 or 11, wherein the membrane filter used in membrane filtration has a pore size of 1 nm to 100 μm.

17. The method for performing membrane-filtration according to claim 16, wherein the membrane filter used in membrane filtration has a pore size of 10 nm to 1 μm.

18. The method for performing membrane-filtration according to claim 16, wherein the membrane filter used in membrane filtration has a pore size of 0.1 μm to 0.5 μm.

* * * * *